US008636994B2

(12) United States Patent
Bossard et al.

(10) Patent No.: US 8,636,994 B2
(45) Date of Patent: *Jan. 28, 2014

(54) POLYMER-BASED COMPOSITIONS AND CONJUGATES OF ANTIMICROBIAL AGENTS

(71) Applicant: Nektar Therapeutics, San Francisco, CA (US)

(72) Inventors: Mary J. Bossard, Madison, AL (US); Stacy Mitchell, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/800,138

(22) Filed: Mar. 13, 2013

(65) Prior Publication Data

US 2013/0195839 A1  Aug. 1, 2013

Related U.S. Application Data

(63) Continuation of application No. 13/593,183, filed on Aug. 23, 2012, now Pat. No. 8,420,068, which is a continuation of application No. 11/402,641, filed on Apr. 11, 2006, now Pat. No. 8,273,339.

(60) Provisional application No. 60/671,000, filed on Apr. 12, 2005.

(51) Int. Cl.
*A61K 31/74* (2006.01)

(52) U.S. Cl.
USPC ..................................................... 424/78.17

(58) Field of Classification Search
None
See application file for complete search history.

(56) References Cited

U.S. PATENT DOCUMENTS

| 3,278,378 A | 10/1966 | Schindler et al. |
| 3,398,056 A | 8/1968 | Zygmunt et al. |
| 4,931,390 A | 6/1990 | Recsei |
| 5,739,208 A | 4/1998 | Harris |
| 5,932,462 A | 8/1999 | Harris et al. |
| 5,955,422 A | 9/1999 | Lin |
| 6,214,966 B1 | 4/2001 | Harris |
| 6,348,558 B1 | 2/2002 | Harris et al. |
| 6,362,254 B2 | 3/2002 | Harris et al. |
| 6,413,507 B1 | 7/2002 | Bentley et al. |
| 6,515,100 B2 | 2/2003 | Harris |
| 6,864,350 B2 | 3/2005 | Harris |
| 7,655,747 B2 | 2/2010 | Harris |

(Continued)

FOREIGN PATENT DOCUMENTS

| EP | 1 025 860 | 8/2000 |
| WO | WO 90/12874 | 11/1990 |

(Continued)

OTHER PUBLICATIONS

Atherton, et al., "Solid Phase Peptide Synthesis using Nα-Fluorenylmethoxycarbonylamino Acid Pentafluorophenyl Esters", J. Chem. Soc. Chem. Commun., pp. 165-166, (1985).

(Continued)

*Primary Examiner* — Paul Dickinson
(74) *Attorney, Agent, or Firm* — Mark A. Wilson

(57) ABSTRACT

Provided herein are water-soluble polymer conjugates and polymer-based compositions of antimicrobial agents. Also provided are methods for synthesizing and administering such conjugates and compositions.

3 Claims, 11 Drawing Sheets

Reverse Phase Analysis the mPEG$_{5,000}$ Da−Lysostaphin (Conjugate A$_{5k}$, pH 6.95) PEGylation Reaction Mixture

(56) References Cited

U.S. PATENT DOCUMENTS

| | | | |
|---|---|---|---|
| 8,273,339 | B2 | 9/2012 | Bossard et al. |
| 8,420,068 | B2 | 4/2013 | Bossard et al. |
| 2002/0006406 | A1 | 1/2002 | Goldstein et al. |
| 2002/0082345 | A1 | 6/2002 | Kozlowski et al. |
| 2003/0215436 | A1* | 11/2003 | Walsh et al. ............... 424/94.62 |
| 2004/0192581 | A1 | 9/2004 | Walsh et al. |
| 2005/0014903 | A1 | 1/2005 | Kozlowski et al. |
| 2006/0239960 | A1 | 10/2006 | Bossard et al. |

FOREIGN PATENT DOCUMENTS

| | | |
|---|---|---|
| WO | WO 95/11924 | 5/1995 |
| WO | WO 01/47562 | 7/2001 |
| WO | WO 01/62299 | 8/2001 |
| WO | WO 01/62827 | 8/2001 |
| WO | WO 03/082926 | 10/2003 |
| WO | WO 2004/060965 | 7/2004 |
| WO | WO 2004/060977 | 7/2004 |
| WO | WO 2004/075923 | 9/2004 |
| WO | WO 2004/089280 | 10/2004 |
| WO | WO 2005/000360 | 1/2005 |
| WO | WO 2005/016240 | 2/2005 |
| WO | WO 2005/089805 | 9/2005 |

OTHER PUBLICATIONS

Beldie, et al., "Bioactive Polymers", Biomaterials, vol. 10, No. 9, pp. 622-624, (1989).

Bentley, et al., "Peg-Linked Artemisinin Antimalarials", Polymer Preprints, vol. 38, No. 1, pp. 584-585, (1997).

Borysowski, et al., "Bacteriophage Endolysins as a Novel Class of Antibacterial Agents", Exp. Biol. Med., vol. 231, pp. 366-377, (2006).

Nash, et al., "Tumour necrosis factor inhibitors", MJA, vol. 183, No. 4, pp. 205-208, (Aug. 15, 2005).

Ouchi, et al., "Design of Antitumor Agent-Terminated Poly(Ethylene Glycol) Conjugate as Macromolecular Prodrug", Polymer Preprints, vol. 38, pp. 582-583, (1997).

Roberts, et al., "Chemistry for peptide and protein PEGylation", Adv. Drug Delivery Reviews, vol. 54, pp. 459-476, (2002).

Schuhardt, et al., "Lysostaphin Therapy in Mice Infected with *Staphylococcus aureus*", J. Bacteriol., vol. 88, pp. 815-816, (1964).

Sims, et al., "A Method for the Estimation of Polyethylene Glycol in Plasma Protein Fractions", Analytical Biochemistry, vol. 107, pp. 60-63, (1980).

Walsh, et al., "Improved Pharmacokinetics and Reduced Antibody Reactivity of Lysostaphin Conjugated to Polyethylene Glycol", Antimicrobial Agents and Chemotherapy, vol. 47, No. 2, pp. 554-558, (Feb. 2003).

Zalipsky, et al., "Attachment of Drugs to Polyethylene Glycols", European Polymer Journal, vol. 19, No. 12, pp. 1177-1183, (1983).

Zalipsky, "Chemistry of polyethylene glycol conjugates with biologically active molecules", Advanced Drug Delivery Reviews, vol. 16, pp. 157-182, (1995).

Zalipsky, et al., "Use of Functionalized Poly(Ethylene Glycol)s for Modification of Polypeptides", Polyethylene Glycol Chemistry: Biotechnical and Biomedical Applications, J.M. Harris, Plenum Press, N.Y., pp. 347-370. (1992).

Zhao, et al., "Novel Degradable Poly(ethylene glycol) Esters for Drug Delivery", Poly(ethylene glycol) Chemistry and Biological Applications, ACS Symposium Series, pp. 458-472, (1997).

PCT International Search Report, PCT Application No. PCT/US2006/013548, filed Apr. 11, 2006, date of mailing May 16, 2007.

PCT Written Opinion of the International Searching Authority, PCT Application No. PCT/US2006/013548, filed Apr. 11, 2006, date of mailing Oct. 25, 2007.

International Preliminary Report, PCT Application No. PCT/US2006/013548, filed Apr. 11, 2006, date of mailing Oct. 25, 2007.

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

NOF Corporation, PEG Derivatives, Phospholipid and Drug Delivery Materials for Pharmaceuticals, 46 pages, Catalogue 2003-$1^{st}$, (Jan. 2003).

NOF Corporation, PEG Derivatives, Phospholipid and Drug Delivery Materials for Pharmaceuticals, 27 pages, Catalogue 2003-$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Office Communication dated Jul. 29, 2008, corresponding to European Application No. 06 749 809.7-1216.

Office Communication dated Aug. 28, 2009, corresponding to European Application No. 06 749 809.7-1216.

Communication corresponding to European Patent Application No. 06 749 809.7-1216 dated Jan. 31, 2011.

Communication corresponding to European Patent Application No. 06 749 809.7-1216 dated Jun. 6, 2011.

European Examination Report corresponding to European Patent Application No. 06 749 809.7-1216 dated Jun. 28, 2011.

\* cited by examiner

Reverse Phase Analysis the mPEG$_{5,000}$ Da-Lysostaphin (Conjugate A$_{5k}$, pH 6.95) PEGylation Reaction Mixture

| Species | Retention Time (min) | Area % |
|---|---|---|
| Native Lysostaphin | 9.390 | 1.11 |
| 1mer | 12.700 | 49.01 |
| 2mer | 14.541 | 42.62 |
| 3mer | 15.933 | 7.24 |

Reverse Phase HPLC of mPEG$_{5,000\,Da}$-Lysostaphin (Conjugate A$_{5k}$, pH 6.95)

Degradation Study of mPEG$_{5,000}$ $_{Da}$-Lysostaphin (Conjugate A$_{5k}$, pH 6.95) Performed at pH 7.35 and 37°C.

Reverse Phase Analysis the mPEG$_{20,000 Da}$-Lysostaphin (Conjugate B$_{20k}$, pH 6.95)
-Containing Composition

| Species | Retention Time (min) | Area % |
|---|---|---|
| Native Lysostaphin | 9.065 | 2.8 |
| 1mer | 12.52 | 93.7 |
| 2mer | 13.827 | 3.5 |

Reverse Phase HPLC of mPEG$_{20,000\,Da}$-Lysostaphin (Conjugate B$_{20k}$, pH 6.95) (1-mer conjugate).

SDS-PAGE Analysis of mPEG$_{20,000\,Da}$-Lysostaphin (Conjugate B$_{20k}$, pH 6.95)

Degradation Study of mPEG$_{20,000\,Da}$-Lysostaphin (Conjugate B$_{20k}$, pH 6.95) performed at pH 7.35 and 37°C.

MALDI-TOF of mPEG$_{30,000\ Da}$-Lysostaphin (Conjugate A$_{30k}$, pH 5.6)

Degradation Study of mPEG$_{30,000\ Da}$-Lysostaphin (Conjugate A$_{30k}$, pH 5.6)
Performed at pH 7.35 and 37°C.

Reverse Phase Analysis the mPEG$_{30,000\ Da}$-Lysostaphin (Conjugate A$_{30k}$, pH 6.9) PEGylation Reaction Mixture Reverse Phase HPLC of mPEG$_{30,000\ Da}$-Lysostaphin (Conjugate A$_{30k}$, pH 6.9)

MALDI-TOF of mPEG$_{30,000\ Da}$-Lysostaphin (Conjugate A$_{30k}$, pH 6.9)

Degradation Study of mPEG$_{30,000\ Da}$-Lysostaphin (Conjugate A$_{30k}$, pH 6.9)
Performed at pH 7.29 and 37°C.

US 8,636,994 B2

POLYMER-BASED COMPOSITIONS AND CONJUGATES OF ANTIMICROBIAL AGENTS

CROSS REFERENCE TO RELATED APPLICATION

This application is a continuation of U.S. patent application Ser. No. 13/593,183, filed Aug. 23, 2012, now U.S. Pat. No. 8,420,068, which is a continuation of U.S. patent application Ser. No. 11/402,641, filed Apr. 11, 2006, now U.S. Pat. No. 8,273,339, which claims the benefit of priority to U.S. Provisional Patent Application Ser. No. 60/671,000, filed Apr. 12, 2005, the disclosures of which are incorporated herein by reference in their entireties.

FIELD OF THE INVENTION

Among other things, one or more embodiments of the present invention relate generally to conjugates comprising an antimicrobial agent (i.e., a moiety having antimicrobial activity) and a polymer. In addition, the invention relates to compositions comprising conjugates, methods for synthesizing conjugates and compositions, and methods for administering compositions.

BACKGROUND OF THE INVENTION

Lysostaphin is a 27-kDa protein produced by *Staphylococcus simulans* biovar staphyloliticus. The protein is a potent endopeptidase that cleaves pentaglycine linkages associated with the bacterial cell wall of nearly all known staphylococcal species (although it is inactive against all other bacterial genera). Thus, upon secretion by *S. simulans*, lysostaphin kills staphylococcal species that may compete with *S. simulans* for nutrients.

In view of its activity against many staphylococcal species (including *S. aureus*), lysostaphin has been tested for possible antibacterial activity in animal models. See Schuhardt et al. (1964) *J. Bacteriol* 88:815-816. Parenteral administration of lysostaphin analogs to treat patients suffering from staphylococcal infections has been described. See U.S. Patent Application Publication No. 2002/0006406.

Because of its relatively short half-file, however, the recommended frequency for dosing lysostaphin analogs can be as often as three times a day. See U.S. Patent Application Publication No. 2002/0006406. Lysostaphin itself is also expected to require relatively frequent injections. Moreover, because lysostaphin is a foreign protein, administration of lysostaphin likely will result in the precipitation of an immune response in humans.

Some have suggested the use of PEGylation technology, or the attachment of a poly(ethylene glycol) derivative to a protein, in order to prolong the antimicrobial agent's in vivo half-life. For example, U.S. Patent Application Publication No. 2003/0215436 describes certain poly(ethylene glycol)-lysostaphin conjugates. The described poly(ethylene glycol) reagents result in specific conjugates having specific structures.

Notwithstanding these described conjugates, however, it remains advantageous to provide conjugates of lysostaphin and other antimicrobials that satisfy one or more of the following: conjugates formed from different polymeric reagents (e.g., PEGs having different structures, reactive groups, and so forth); conjugates formed from PEG derivatives having different weight average molecular weights; and conjugates formed from a variety of antimicrobial agents.

Thus, there remains a need in the art to provide additional conjugates of water-soluble polymers and antimicrobial agents. Among other things, one or more embodiments of the present invention is therefore directed to such conjugates as well as to compositions comprising the conjugates and related methods as described herein, which are believed to be new and completely unsuggested by the art.

SUMMARY OF THE INVENTION

Accordingly, in one or more embodiments of the invention, a conjugate is provided comprising a residue of an antimicrobial agent attached to a water-soluble polymer by non-degradable linkage.

Further, in one or more embodiments of the invention, a conjugate is provided comprising a residue of an antimicrobial agent attached to a water soluble-polymer by a degradable linkage.

The conjugates described herein advantageously reduce immunogenicity. Equally important, the present conjugates and compositions require decreased frequency of dosing compared to previously described antimicrobial compositions absent such a water-soluble polymer. Thus, the conjugates and compositions provided herein advantageously decrease the number of painful injections while simultaneously lessening the likelihood of initiating an immunogenic response.

When the conjugate comprises a non-degradable linkage, the linkage can be selected from the group consisting of an amide linkage, secondary amine linkage, carbamate linkage, thioether linkage, and disulfide linkage. The non-degradable linkage can, however, be a non-degradable linkage other than these and the invention is not limited in this regard.

When the conjugate comprises a degradable linkage, it is preferred that the degradable linkage is either a hydrolyzable linkage or an enzymatically degradable linkage. Exemplary hydrolyzable linkages include linkages that include a hydrolyzable moiety such as a carboxylate ester, a phosphate ester, a carbamate, an anhydride, an acetal, a ketal, an acyloxyalkyl ether, an imine, an orthoester, a thioester, a thiolester, or a carbonate. The degradable linkage can, however, be a degradable linkage other than these and the invention is not limited in this regard.

In one or more embodiments of the invention, a conjugate of the invention possesses the following structure:

$$[\text{Poly-}[L_D]_{\overline{k}}-(\text{LY}) \qquad \text{I}$$

where POLY is a water-soluble polymer, $L_D$ is a degradable linkage, LY is a residue of an antimicrobial agent, and (k) corresponds to the number of reactive sites on the antimicrobial agent to which a water-soluble polymer is covalently attached. Each water-soluble polymer in the conjugate is independently selected (i.e., each water-soluble polymer can be the same or different than any other water-soluble polymer in the conjugate), although preferably, each of the water-soluble polymers in the conjugate is the same. Typically, (k) ranges from about 1 to about 8, that is to say, (k) is a positive, whole number integer preferably selected from the group consisting of 1, 2, 3, 4, 5, 6, 7 and 8. More preferably, (k) is 1, 2, 3, or 4, or even more preferably, (k) is 1. Exemplary reactive sites to which a water-soluble polymer can be attached include, without limitation, the N-terminal, the C-terminal, an amino group (e.g., associated with the side chain of a lysine residue), a hydroxyl group, and a thiol group (e.g. associated with side chain of a cysteine residue).

In one or more embodiments of the present invention, the water-soluble polymer associated with a conjugate or composition is a polyethylene glycol.

The water-soluble polymer, e.g., polyethylene glycol, typically has a molecular weight falling within one of the following ranges: from about 500 Daltons to about 100,000 Daltons; from about 2,000 Daltons to about 85,000 Daltons; from about 5,000 Daltons to about 60,000 Daltons; from about 10,000 Daltons to about 50,000 Daltons; and from about 15,000 Daltons to about 40,000 Daltons; and may possess any of a number of architectures (e.g., linear, branched, forked, and the like).

Antimicrobial agents for use herein are peptidyl in nature (although such antimicrobial agents can include one or more non-peptidyl moieties). Exemplary antimicrobial agents include preprolysostaphin, prolysostaphin, mature lysostaphin, and mature active lysostaphin.

Generally, the $L_D$ possesses a length satisfying one or more of the following ranges: from about 1 to about 20 atoms; from about 2 to about 15 atoms; and from about 3 to about 10 atoms. Specific atom lengths for a typical $L_D$ include 1, 2, 3, 4, 5, 6, 7, 8, 9, 10, 11, 12, 13, 14, 15, 16, 17, 18, 19, and 20.

In one or more embodiments of the invention, a conjugate comprising one of the following generalized structures:

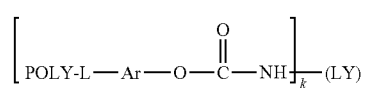

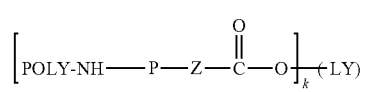

where L is either —O— or —NH—C(O), Ar is an aromatic group, such as an ortho, meta, or para-substituted phenyl, —NH— in structure II is an amino residue from an antimicrobial moiety, P is a spacer, Z is —O—, —NH—, or —CH$_2$—, and —O—[adjacent to "(LY)"] in structure III is the residue of a hydroxyl group-containing antimicrobial agent. In a more particular embodiment, in structure III, P, when taken together with —NH—P—Z—C(O)—, is the residue of a naturally or non-naturally occurring amino acid.

In yet an additional embodiment, a conjugate in accordance with the invention is characterized by the structure:

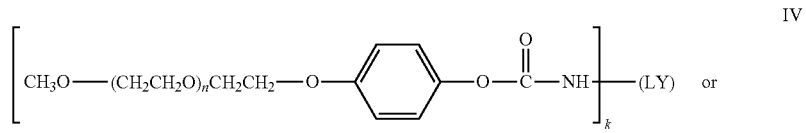

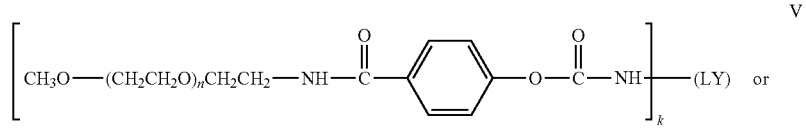

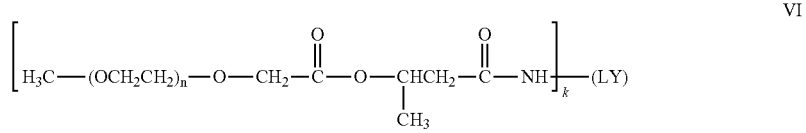

where n ranges from 2 to about 3400 and (LY) is as previously defined.

Also forming part of the invention are conjugates of multi-armed water soluble polymers.

In or more embodiments of multi-armed water soluble polymers, the multi-armed polymer comprises a central core from which extends three or more polymer arms which are typically homopolymeric or co-polymeric.

In yet another embodiment of a multi-armed polymer conjugate in accordance with the invention, each polymer arm comprises a copolymer comprising an inner polypeptide segment covalently attached to a central core and an outer hydrophilic polymer segment covalently attached to the polypeptide segment.

Exemplary conjugates in accordance with this aspect of the invention will generally comprise the following structure:

VII wherein R is a core molecule, POLY is a water-soluble polymer, $L_D$ is a degradable linkage, LY is a residue of a lysostaphin moiety, and y ranges from about 3 to 15.

Alternatively, the conjugate may comprise the structure:

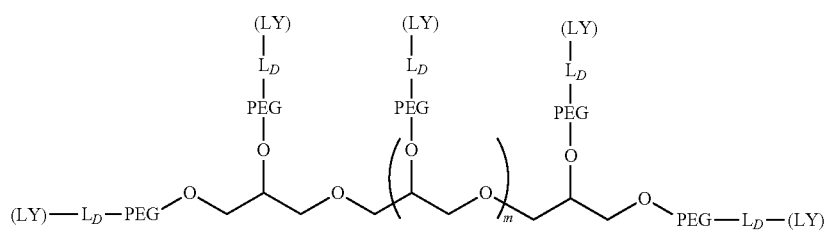
VIII where m is selected from 3, 4, 5, 6, 7, and 8, and each of $L_D$ and LY is a previously defined.

In yet a further and more specific embodiment, a conjugate of this type may correspond to the structure:

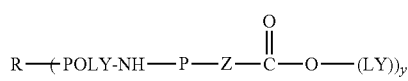
IX where P is a spacer, Z is —O—, —NH—, or —CH$_2$—, and —O— is a residue of a hydroxyl-containing lysostaphin moiety. In a preferred embodiment, P, when taken together with —NH—P—Z—C(O)— is a residue of a naturally or non-naturally occurring amino acid.

In yet another aspect, the invention encompasses a composition comprising a plurality of mono-polymer LY conjugates, meaning LY conjugates each having one water-soluble polymer covalently attached to the LY, but at different reactive sites or positions thereupon (wherein "LY" represents a lysostaphin moiety).

In another aspect of the invention, a lysostaphin moiety is admixed with a hydrogel, more preferably, a hydrolytically degradable hydrogel, i.e., one that degrades under physiological conditions. Such hydrogels may be cross-linked or non-crosslinked. In a preferred embodiment, the hydrogel is a non-reverse gelation hydrogel comprising a lysostaphin moiety, and as one of the gel components, a poly(alkylene oxide). In a particular embodiment, the lysostaphin moiety is in the form of a water-soluble polymer conjugate. Alternatively, the antimicrobial agent is optionally covalently attached to one or more gel components.

Also forming part of the invention is a method for making a polymer conjugate. The method comprises the step of contacting, under conjugation conditions, an antimicrobial agent (e.g., lysostaphin moiety) with a polymeric reagent to form a conjugate. Preferably such a conjugate comprises a degradable linkage.

In yet a further aspect, provided is a method for preparing a non-reverse gelation hydrogel comprising an antimicrobial agent (e.g., a lysostaphin moiety). Such a method includes the step of contacting suitable hydrogel precursor reagents with one another and with the antimicrobial agent under conditions effective to promote gelling of the precursor reagents, to thereby form a non-reverse gelation hydrogel having the antimicrobial agent entrapped therein. The antimicrobial agent is either in conjugated or unconjugated form, and the hydrogel precursor reagents do not exhibit reverse gelation properties.

In still another embodiment of the invention, compositions are provided comprising a conjugate of the invention in combination with a pharmaceutically acceptable excipient. The compositions encompass all types of formulations and in particular those that are suited for injection, such as powders that can be reconstituted, as well as liquids (e.g., suspensions and solutions).

In an additional embodiment of the invention, a method of inhibiting the growth of staphylococcal organisms is provided. In the method, a conjugate or pharmaceutical composition as described herein is administered to a patient. Typically, the step of administering is effected by injection (e.g., intramuscular injection, intravenous injection, subcutaneous injection, and so forth).

Additional objects, advantages and novel features of the invention will be set forth in the description that follows, and in part, will become apparent to those skilled in the art upon reading the following, or may be learned by practice of the invention.

DETAILED DESCRIPTION OF THE INVENTION

Figure 1:
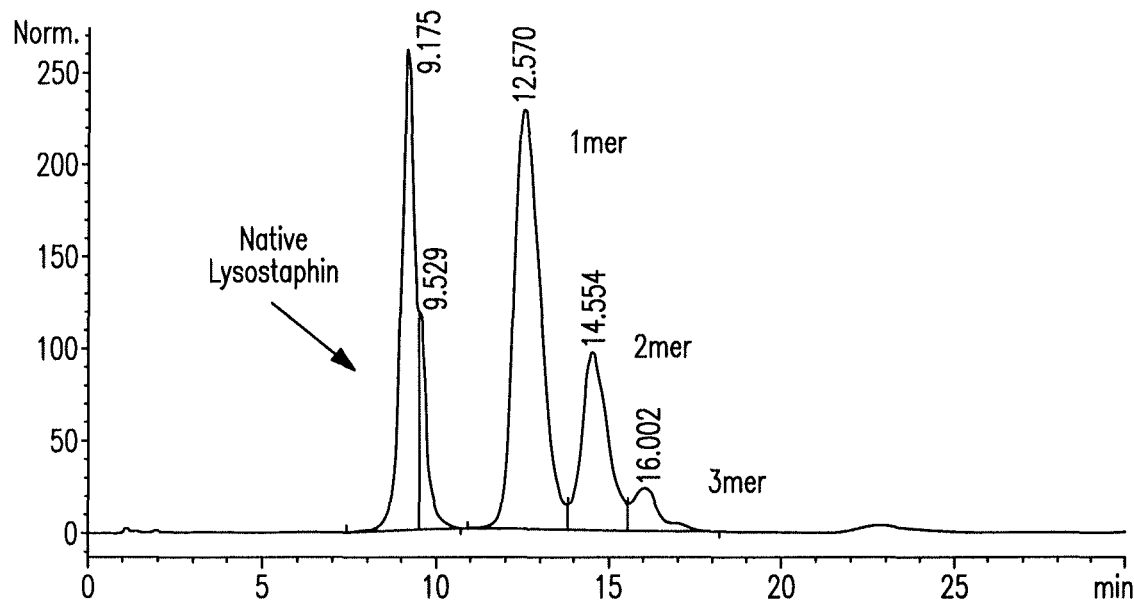
FIG. 1 corresponds to the results of a reverse phase HPLC analysis of mPEG$_{5,000\ Da}$-lysostaphin PEGylation reaction mixture, as described in Example 1.

Before describing the present invention in detail, it is to be understood that this invention is not limited to the particular polymers, hydrogels, synthetic techniques, antimicrobial agents, and the like, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to a "an optional excipient" refers to a single optional excipient as well as two or more of the same or different optional excipients, and the like.

In describing and claiming the present invention, the following terminology will be used in accordance with the definitions described below.

"PEG," "polyethylene glycol" and "poly(ethylene glycol)" as used herein, are interchangeable and meant to encompass any water-soluble poly(ethylene oxide). Typically, PEGs for use in accordance with the invention comprise the following structure "—(OCH$_2$CH$_2$)$_n$—" where (n) ranges from 2 to about 4000. As used herein, the term "PEG" may also refer to the particular structures "—CH$_2$CH$_2$—O(CH$_2$CH$_2$O)$_n$—CH$_2$CH$_2$-" or "—(OCH$_2$CH$_2$)$_n$O—," depending upon whether or not the terminal oxygens have been displaced.

Throughout the specification and claims, it should be remembered that the term "PEG" includes structures having various terminal or "end capping" groups and so forth. The term "PEG" refers to a polymer that contains a majority, that is to say, greater than 50%, of —OCH$_2$CH$_2$— repeating subunits. With respect to specific forms, the PEG can take any number of a variety of molecular weights, as well as structures or geometries, such as "branched," "linear," "forked," "multifunctional," and the like, to be described in greater detail below.

The terms "end-capped" and "terminally capped" are used interchangeably herein to refer to a terminal or endpoint of a polymer having an end-capping moiety. Typically, although not necessarily, the end-capping moiety comprises a hydroxy or C$_{1-20}$ alkoxy group or benzyloxy group, more preferably a C$_{1-10}$ alkoxy group, and still more preferably a C$_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in CH$_3$(OCH$_2$CH$_2$)$_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes) labels, metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water soluble" as in a "water-soluble polymer" polymer is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight, in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis, MALDI-TOF, or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

By overall atom length, e.g., in the context of a linker, is meant the number of atoms in a single chain, not counting substituents. For instance, —$CH_2$— counts as one atom with respect to overall linker length, —$CH_2CH_2O$— counts as 3 atoms in length, and a non-linear group such as a phenyl ring counts as 4 atoms in length.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "linkage" or "linker" are used herein to refer to an atom or a collection of atoms optionally used to link interconnecting moieties such as a terminus of a polymer segment and an antimicrobial agent (e.g., a lysostaphin moiety). A linker may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucelophilic group" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient" or "carrier" refers to an excipient that may optionally be included in the compositions of the invention and that causes no significant adverse toxicological effects to the patient. "Pharmacologically effective amount," "physiologically effective amount,"

and "therapeutically effective amount" are used interchangeably herein to mean the amount of a conjugate or composition (e.g., a hydrogel) that is needed to provide a desired level of the conjugate of the antimicrobial (or unconjugated antimicrobial when a degradable linkage is used in the microbial conjugate) in the bloodstream or in the target tissue. The precise amount will depend upon numerous factors, e.g., the particular antimicrobial agent, the components and physical characteristics of the therapeutic composition, intended patient population, individual patient considerations, and the like, and can readily be determined by one skilled in the art, based upon the information provided herein.

"Branched," in reference to the geometry or overall structure of a water-soluble polymer, refers to a water-soluble polymer having two or more polymer "arms" extending from a branch point. A branched polymer may possess two water-soluble polymer arms, three water-soluble polymer arms, four water-soluble polymer arms, six water-soluble polymer arms, eight water-soluble polymer arms or more. A subset of branched water-soluble polymers are multi-armed polymers, that is to say, polymers having three or more water-soluble arms extending from a central core.

A "branch point" refers to a bifurcation point comprising one or more atoms at which a polymer or linking group splits or branches from a linear structure into one or more additional polymer arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

A functional group in "protected form" refers to a functional group bearing a protecting group. As used herein, the term "functional group" or any synonym thereof is meant to encompass protected forms thereof. Representative protecting groups are described in, Greene, T., Wuts, P. G., "Protective Groups in Organic Synthesis", 3$^{rd}$ Ed., John Wiley & Sons, Inc., 1999.

"Multi-functional" means a polymer having 3 or more functional groups contained therein, where the functional groups may be the same or different. Multi-functional polymeric reagents will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

An "antimicrobial agent" is an agent that deters or inhibits the growth and/or multiplication of bacteria. For use herein, the antimicrobial agent is a peptide or a modified peptide, such as a hybrid fusion protein, or other chimeric peptide, having at least one electrophilic group or nucleophilic group suitable for reaction with a polymeric reagent. The term "antimicrobial agent" encompasses both the antimicrobial agent prior to and following conjugation.

A "hydrogel" is a material that absorbs a solvent (e.g. water), undergoes rapid swelling without discernible dissolution, and maintains three-dimensional networks capable of reversible deformation. Hydrogels may be uncrosslinked or crosslinked. Covalently (chemically) crosslinked networks of hydrophilic polymers, such as PEG, can form hydrogels (or aquagels) in the hydrated state. Uncrosslinked hydrogels are typically block copolymers having hydrophilic and hydrophobic regions. These uncrosslinked materials can form hydrogels when placed in an aqueous environment, due to physical crosslinking forces resulting from ionic attractions, hydrogen bonding, Van der Waals forces, and so forth. They are able to absorb water but do not dissolve due to the presence of hydrophobic and hydrophilic regions.

"Substantially" or "essentially" means nearly totally or completely, for instance, 95% or greater of some given quantity.

The term "patient," refers to a living organism suffering from or prone to a condition that can be prevented or treated by administration of an active agent of the invention (e.g., conjugate), and includes both humans and animals.

"Optional" or "optionally" means that the subsequently described circumstance may or may not occur, so that the description includes instances where the circumstance occurs and instances where it does not.

Amino acid residues in peptides are abbreviated with either single letter abbreviations or the corresponding amino acid abbreviations as follows:

| | | |
|---|---|---|
| F | Phe | Phenylalanine |
| L | Leu | Leucine |
| I | Ile | Isoleucine |
| M | Met | Methionine |
| V | Val | Valine |
| S | Ser | Serine |
| P | Pro | Proline |
| T | Thr | Threonine |
| A | Ala | Alanine |
| Y | Tyr | Tyrosine |
| H | His | Histidine |
| Q | Gln | Glutamine |
| N | Asn | Asparagine |
| K | Lys | Lysine |
| D | Asp | Aspartic Acid |
| E | Glu | Glutamic Acid |
| C | Cys | Cysteine |
| W | Trp | Tryptophan |
| R | Arg | Arginine |
| G | Gly | Glycine |

As stated previously, the present invention provides compositions and methods for sustained delivery of antimicrobial agents (such as a lysostaphin moiety). Described herein are exemplary polymers, conjugates and compositions for prolonging the half-life of relatively short-acting antimicrobial agents, particularly those that are peptide-based, whilst also maintaining at least a measurable, and more preferably, a significant degree of their antimicrobial activity upon administration. In certain instances, preferred are polymer conjugates having one or more hydrolyzable linkages designed to release the polymer portion of the conjugate in-vivo, or degradable hydrogel-based compositions, to be described in greater detail herein. In particular for drugs such as antimicrobial agents, conjugates possessing one or more degradable linkages possess the advantage of having both a prolonged circulating half-life, and exhibiting bioactivity in vivo due to the degradable nature of the polymer attachment, since the polymer is released from the antimicrobial agent upon hydrolysis. Thus, in such embodiments, the impact of the size and position of polymer attachment on the ability of the antimicrobial agent is not of particular concern, since the polymer portion of the conjugate falls off in the body to release the native antimicrobial agent.

Although any peptidyl antimicrobial agent can be used in accordance with the present invention, it is particularly preferred that the antimicrobial agent is a lysostaphin moiety. Preferred lysostaphin moieties will have at least about 50% sequence homology with preprolysostaphin (i.e., amino acid residues 1-389 of SEQ ID NO. 1), prolysostaphin (i.e., amino acid residues 37-389 of SEQ ID NO. 1), lysostaphin (i.e., amino acid residues 140-389 of SEQ ID NO. 1), or mature active lysostaphin (i.e., amino acid residues 144-389 of SEQ ID NO. 1). Preferred water-soluble polymer attachment sites include the amino group of lysine side chain(s), the N-terminal, the C-terminal, and hydroxyl groups present on tyrosine, threonine, or serine. In addition, the antimicrobial agent can advantageously be nisin.

Biologically active fragments, deletion variants, substitution variants or addition variants of any of the foregoing that maintain at least some degree of antimicrobial activity can also be used. Such antimicrobial agents can be made recombinantly or using synthetic methods well known in the art.

The antimicrobial agents can advantageously be modified, if necessary, to include one or more amino acid residues such as, for example, lysine, cysteine and/or arginine, in order to provide facile attachment of the polymer to an atom within the side chain of the added amino acid. Techniques for adding amino acid residues are well known to those of ordinary skill in the art. Reference is made to J. March, Advanced Organic Chemistry: Reactions Mechanisms and Structure, $4^{th}$ Edition.

Any of the above antimicrobial agents can be prepared using one or more of the following synthetic approaches well known in the art for the synthesis and preparation of polypeptides in general. For example, an antimicrobial agent may be synthesized using conventional stepwise solution or solid phase synthesis, fragment condensation, F-MOC or T-BOC chemistry, e.g., as described in *Chemical Approaches to the Synthesis of Peptides and Proteins*, William et al., Eds., 1997, CRC Press, Boca Raton Fla., and in references cited therein; in *Solid Phase Peptide Synthesis: A Practical Approach*, Atherson & Sheppard, Eds., 1989, IRL Press, Oxford, England, and in Sheppard, R. C. et al., *J. Chem. Soc. Chem. Comm.*, pp. 165-166 (1985)), using, for example, an Advanced Chemtech model 200 available from Advanced Chemtech., Louisville, Ky., a Millipore 9050+ available from Millipore, Bedford Mass., or other available instrumentation.

In addition, the antimicrobial agent may be recombinantly engineered by incorporating cDNA coding sequences into functional viral or circular plasmid DNA vectors. The vectors or plasmids are then used to transfect or transform selected microorganisms. The transformed or transfected microorganisms are cultured under conditions that are conducive to express vector-borne DNA sequences, followed by isolation of the desired peptides from the growth medium. See, for example U.S. Pat. No. 5,955,422. Vectors that may be used include those derived from recombinant bacteriophage DNA, plasmid DNA or cosmid DNA. For example, plasmid vectors such as pcDNA3, pBR322, pUC 19/18, pUC 118, 119 and M13 mp series of vectors may be used. Bacteriophage vectors include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, and pNNI.

Recombinant viral vectors may also be used including those derived from herpes virus, retroviruses, vaccinia viruses, adenoviruses, or baculovirus.

The antimicrobial agent may also be prepared using standard recombinant DNA technology techniques that are well known in the art, such as those described in Sambrook, et al., *Molecular Cloning: A Laboratory Manual, 2nd edition*, (Cold Spring Harbor Press, Cold Spring Harbor, N.Y.) or in Ausubel et al., *Current Protocols in Molecular Biology*, both of which are herein incorporated by reference. An illustrative method for preparing lysostaphin is described in U.S. Pat. No. 4,931,390.

After cleavage and deprotection, the antimicrobial agent may be purified by, for example, ion exchange chromatography, gel electrophoresis, affinity chromatography, size exclusion chromatography, precipitation, and the like. Alternatively, normal or reverse-phase HPLC may be employed to purify/separate full length polypeptides from smaller fragments.

Amino acid sequences of an antimicrobial agent can be confirmed and identified by using standard amino acid analysis, as well as by using manual or automated Edman degradation and determination of each amino acid, using for example, automated amino acid sequencers such as those manufactured by Applied Biosystems. Suitable automated sequencers include the Applied Biosystems 476A Protein Sequencer or the Procise 494 Protein Sequencer. Both instruments use standard gas phase or pulsed liquid Edman degradation chemistry. HPLC analysis or mass spectrometry may also be used to confirm the identity of a given antimicrobial agent.

As previously discussed, one or more embodiments of the invention are directed to conjugates of an antimicrobial agent, such as lysostaphin, attached to a water-soluble polymer, often designated herein simply as POLY. With respect to the water-soluble polymer, the water-soluble polymer is nonpeptidic, nontoxic, non-naturally occurring and biocompatible. A substance is generally considered biocompatible if the beneficial effects associated with use of the substance alone or with another substance (e.g., an active agent such an antimicrobial agent) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer of the invention is both biocompatible and nonimmunogenic.

Examples of such polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and combinations of any of the foregoing. A polymer of the invention may be a homopolymer, alternating copolymer, random copolymer, block copolymer, alternating tripolymer, random tripolymer, or a block tripolymer made up of monomers of any of the preceding polymers. Preferably, the polymer is a copolymer, or, more preferably, is a homopolymer, e.g., of polyethylene glycol. Although much of the discussion herein is focused upon PEG as an illustrative water-soluble polymer, the discussion and structures presented herein are meant to encompass any of the water-soluble polymers described above. More specifically, for exemplary structures and figures demonstrating "PEG" as the water-soluble polymer, the term "PEG" is also meant to be substituted with any of the alternative water-soluble polymers described herein, such that the structures and figures provided herein explicitly extend to such alternative water-soluble polymers.

The polymer per se, prior to conjugation, is typically characterized as having from 2 to about 300 termini, more preferably from about 2 to about 25 termini, even more preferably having 2, 3, 4, 5, 6, 7, 8, 9, or 10 termini.

The polymer is not limited to a particular structure and can be linear (e.g., end-capped PEG or linear bifunctional PEG), branched or multi-armed. Typically, PEG and other water-soluble polymers, prior to conjugation with an antimicrobial agent, are activated with a suitable activating group appropriate for coupling to a desired site on the antimicrobial agent. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), in Zalipsky (1995) *Advanced Drug Reviews* 16:157-182, in Roberts, M. et al., "*Chemistry for Peptide and Protein PEGylation*", Advanced Drug Delivery Reviews 54 (2002): 459-476, and in "*Nektar Advanced PEGylation: Polyethylene Glycol and Derivatives for Advanced PEGylation*", Catalog 2004.

Typically, the weight average molecular weight of the non-peptidic water soluble polymer in the conjugate is from about 100 Daltons to about 150,000 Daltons. Exemplary ranges, however, include weight-average molecular weights in the range of about 500 Daltons to about 100,000 Daltons, in the range of about 2,000 Daltons to about 90,000 Daltons, in the range of about 5,000 Daltons to about 85,000 Daltons, in the range of about 10,000 Daltons to about 50,000 Daltons, and in the range of about 15,000 Daltons to about 40,000 Daltons.

High molecular weight polymers, e.g., having a molecular weight greater than one or more of the following values are preferred when the water-soluble polymer is covalently attached to an antimicrobial agent by means of a hydrolysable linkage: about 20,000 Daltons or more; about 30,000 Daltons or more; about 40,000 Daltons or more; about 50,000 Daltons or more; and about 60,000 Daltons or more. In one embodiment, use of a high molecular weight and/or branched degradable polymer is preferred, since due to spatial constraints on the polypeptidyl antimicrobial agent, it may be possible to covalently attach only one or two molecules of high molecular weight polymer to the antimicrobial agent. In this way, formation of a hydrolyzable, 1-mer conjugate (i.e., having only one water-soluble polymer molecule covalently attached to the antimicrobial agent) or 2-mer conjugate, is favored. This can advantageously lead to higher yields, along with a cleaner conjugate synthesis and subsequent separation, purification, and characterization, due to the lack of formation of multiple conjugate species, although different PEG-mers (e.g., 2-mers, 3-mers, 4-mers, and so forth) are separable as described in greater detail below. Moreover, when considering the action of the conjugate in vivo, hydrolysis of a 1-mer may be particularly advantageous, since only a single hydrolysis reaction is involved, i.e., a hydrolysis effective to release the antimicrobial agent and the water-soluble polymer, in contrast to the degradable, covalent attachment of a water-soluble polymer to multiple reactive sites upon the antimicrobial agent, or, alternatively, multiple antimicrobial agents covalently attached to a multi-armed, water-soluble polymer, where release of the water-soluble polymer or of the drug is complicated by the kinetics involved in multiple hydrolysis steps and intermediate species. Although the use of a degradable, high molecular weight water-soluble polymer may, in certain instances, offer certain advantages over alternative conjugate structures or architectures, that is not to say that alternative embodiments, such as the use of smaller polymers, either singly or multiply attached to an antimicrobial agent, or other additional embodiments as described herein, are without their own associated advantages, to be described in greater detail below.

Exemplary weight average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched or other multi-arm versions of the water-soluble polymer (e.g., a branched 40,000 Dalton water-soluble polymer having two 20,000 Dalton water-soluble polymer "arms") having a total molecular weight of any of the foregoing can also be used.

In instances in which the polymer is PEG, the PEG will typically comprise a number of ($OCH_2CH_2$) monomers. As used throughout the description, the number of repeat units is identified by the subscript "n" in "($OCH_2CH_2$)$_n$." Thus, the value of (n) typically falls within one or more of the following ranges: from 2 to about 3400, from about 100 to about 2,300, from about 100 to about 2,270, from about 136 to about 2,050, from about 225 to about 1,930, from about 450 to about 1,930, from about 1,200 to about 1,930, from about 568 to about 2727, from about 660 to about 2730, from about 795 to about 2730, from about 909 to about 2730, and from about 1,200 to about 1,900. For any given polymer in which the molecular weight is known, it is possible to determine the number of repeat units (i.e., "n") by dividing the total molecular weight of the polymer by the molecular weight of the repeat unit.

One particularly preferred polymer for use in the invention is an end-capped polymer, that is, a polymer having at least one terminus capped with a relatively inert group, such as a lower $C_{1-6}$ alkoxy group or a benzyloxy group, although a hydroxyl group can also be used. When the polymer is PEG, for example, it is preferred in many instances to use a methoxy-PEG (commonly referred to as mPEG), which is a form of PEG, typically linear, wherein one terminus of the water-soluble polymer is a methoxy (—$OCH_3$) group, while the other terminus is a hydroxyl or other functional group that can be optionally chemically modified.

The structure of an mPEG can be: $CH_3O$—($CH_2CH_2O$)$_n$—$CH_2CH_2$—, where the value of (n) is as described above.

Alternatively, rather than being end-capped, a polymeric reagent (and corresponding product) may possess a dumbbell-like or bifunctional linear structure, such that the resulting conjugate is one in which antimicrobial agents are interconnected by a central linear POLY, e.g., PEG. More specifically, in one embodiment, such a conjugate is represented by the structure "(antimicrobial agent)-PEG-(antimicrobial agent)," where the antimicrobial agents may be the same or different. Preferably, a conjugate of the invention is one where the water-soluble polymer, POLY, is covalently attached to an antimicrobial agent selected from the group consisting of preprolysostaphin, prolysostaphin, lysostaphin and mature active lysostaphin.

A polymer for use in the invention may possess 2 arms, 3 arms, 4 arms, 5 arms, 6 arms, 7 arms, 8 arms or more. Multi-armed polymers can be used to form conjugates, or alternatively, can be used to form hydrogels, and may possess anywhere from 2 to 300 or so reactive termini.

In one embodiment of the invention, preferred are branched water-soluble polymers having 2 or 3 water-soluble polymer arms. An illustrative branched POLY, as described in U.S. Pat. No. 5,932,462, corresponds to the structure:

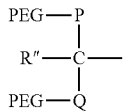

In this representation, R" is a nonreactive moiety, such as H, methyl or a PEG, and P and Q are nonreactive linkages. In the above particular branched configuration, the branched polymer segment possesses a single reactive site extending from the "C" branch point for positioning of the antimicrobial agent, optionally via a linker, which may optionally include a degradable linkage.

In an illustrative embodiment, the branched PEG polymer segment is methoxy poly(ethylene glycol) disubstituted lysine with a single attachment site for covalent attachment to an antimicrobial agent. Depending upon the site of attachment on the antimicrobial agent, the reactive ester group of the disubstituted lysine may be further modified or activated to form a functional group suitable for reaction with a target group on the antimicrobial agent.

Branched PEGs having the above-described generalized structure for use in the present invention will typically have fewer than four PEG arms, and more preferably, will have two or three PEG arms. Such branched PEGs offer the advantage of having a single reactive site, coupled with a larger, more dense polymer cloud than their linear PEG counterparts. One particular type of branched PEG antimicrobial agent conjugate corresponds to the structure: (MeO-PEG-)$_i$G-, where i equals 2 or 3, and G is a lysine or other suitable amino acid residue, with a site suitable for attachment to an antimicrobial agent.

Additional branched PEGs for use in the present invention include those described in International Patent Application Publication No. WO 2005/000360. For instance, an additional branched polymer for preparing an antimicrobial agent conjugate possesses the structure below,

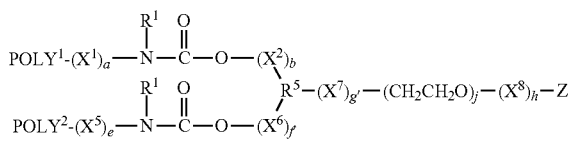

where POLY$^1$ is a water-soluble polymer; POLY$^2$ is a water-soluble polymer; (a) is 0, 1, 2 or 3; (b) is 0, 1, 2 or 3; (e) is 0, 1, 2 or 3; (f) is 0, 1, 2 or 3; (g') is 0, 1, 2 or 3; (h) is 0, 1, 2 or 3; (j) is 0 to 20; each R$^1$ is independently H or an organic radical selected from the group consisting of alkyl, substituted alkyl, alkenyl, substituted alkenyl, alkynyl, substituted alkynyl, aryl and substituted aryl; X$^1$, when present, is a first spacer moiety; X$^2$, when present, is a second spacer moiety; X$^5$, when present, is a fifth spacer moiety; X$^6$, when present, is a sixth spacer moiety; X$^7$, when present, is a seventh spacer moiety; X$^8$, when present, is an eighth spacer moiety; R$^5$ is a branching moiety; and Z is a reactive group for coupling to an antimicrobial agent, optionally via an intervening spacer. Preferably, POLY$^1$ and POLY$^2$ in the preceding branched polymer structure are identical, i.e., are of the same polymer type (structure) and molecular weight.

A representative branched water-soluable polymer falling into the above classification, suitable for use in the present invention is:

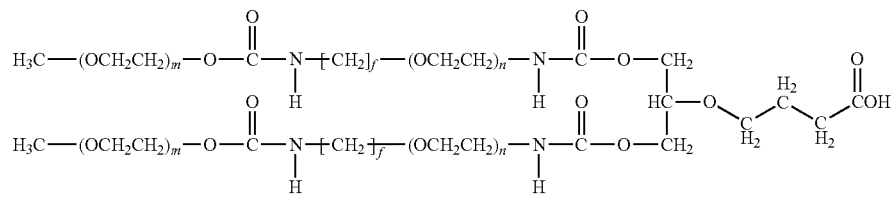

where (m) is 2 to 4000, and (f) is 0 to 6 and (n) is 0 to 20.

Branched water-soluble polymers useful in preparing a conjugate or hydrogel of the invention additionally include those represented more generally by the formula R(POLY)$_y$, where R is a central or core molecule from which extends two or more POLY (i.e., water-soluble polymer such as PEG) arms. The variable "y" represents the number of POLY arms, where each of the water-soluble polymer arms can independently be end-capped or alternatively, possess a reactive functional group at its terminus. A more explicit structure in accordance with this embodiment of the invention possesses the structure, R(POLY-Z)$_y$, where each Z is independently an end-capping group, or a reactive group, e.g., suitable for reaction with a cross-linker or with an antimicrobial agent. In yet a further embodiment when Z is a reactive group, upon reaction with, e.g., either a cross-linker or an antimicrobial agent, the resulting linkage can be hydrolytically stable, or alternatively, may be degradable, i.e., hydrolyzable. Typically, at least one water-soluble polymer arm possesses a terminal functional group suitable for reaction with an antimicrobial agent. Branched PEGs such as those represented generally by the formula, R(PEG)$_y$, possess two water-soluble polymer arms to about 300 polymer arms (i.e., y ranges from 2 to about 300). Preferably, such branched PEGs possess from 2 to about 25 polymer arms, more preferably from 2 to about 20 polymer arms, and even more preferably from 2 to about 15 polymer arms, or from 3 to about 15 polymer arms or fewer. Most preferred are multi-armed polymers having 3, 4, 5, 6, 7 or 8 arms.

Preferred core molecules in branched PEGs as described above are polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

A representative multi-arm structure corresponding to a multi-armed, water-soluble polymer conjugate of the invention is shown below, where "y" preferably ranges from about 3 to about 8, R is as defined above, and L is a linker that covalently attaches each polymer arm to the antimicrobial agent, optionally via a hydrolyzable linkage. As will be described in more detail in the linker section below, although any of a number of linkages can be used to covalently attach a polymer or polymer arm to an antimicrobial agent, in certain instances, the linkage is preferably degradable, designated herein as $L_D$, that is to say, contains at least one bond or moiety that hydrolyzes under physiological conditions, e.g., an ester, hydrolyzable carbamate, carbonate, or other such group.

where LY, R, POLY, y and L are as previously defined.

Additional multi-arm, water-soluble polymers useful for forming a multi-arm antimicrobial agent-conjugate or hydrogel of the invention include multi-arm PEGs available from Nektar Therapeutics (Huntsville, Ala.). Preferred multi-armed activated polymers for use in the method of the invention correspond to the following structure, where E represents a reactive group suitable for coupling to an antimicrobial agent. In one embodiment, E is preferably an —OH (for reaction with an antimicrobial agent carboxy group or equivalent), a carboxylic acid or equivalent, or a carbonic acid (for reaction with antimicrobial agent —OH groups), or an amino group (for reaction with a C-terminal).

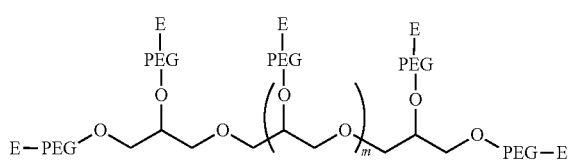

PEG is —(CH$_2$CH$_2$O)$_n$CH$_2$CH$_2$—, and m is selected from the group consisting of 3, 4, 5, 6, 7, and 8. Of course, the corresponding antimicrobial agent-water-soluble polymer conjugate product possesses the structure shown above with the exception that the reactive group, E, is replaced by "-L-(LY)" when the antimicrobial agent is "LY", where L represents a linkage formed by reaction of E and a reactive group present on the antimicrobial agent. As discussed previously, in certain embodiments, preferred linkages are ester, carboxyl and hydrolyzable carbamate, such that the water-soluble polymer-portion of the conjugate is hydrolyzed in vivo to release the antimicrobial agent and the polymer. In such instances, the linker L is designated as $L_D$.

Alternatively, the polymer conjugate may possess an overall forked structure. An example of a forked PEG corresponds to the following generalized structure, where the first structure represents an activated forked PEG and the second structure represents a forked antimicrobial agent polymer conjugate:

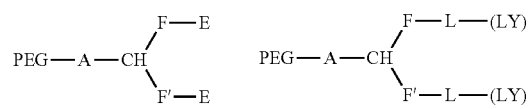

where PEG is any of the forms of PEG described herein, E is a reactive group suitable for covalent coupling with an antimicrobial agent, A is a linking group, preferably a hydrolytically stable linkage such as oxygen, sulfur, or —C(O)—NH—, F and F' are hydrolytically stable spacer groups that are optionally present, and L is as defined above. In a preferred embodiment, the linker L contains at least one hydrolyzable functional group. In the conjugate structure to the right, the antimicrobial agents can be the same or different. As in the previous embodiment, although not shown explicitly, also contemplated is a forked structure where one of the antimicrobial agents is replaced by another antimicrobial agent. Exemplary linkers and spacer groups corresponding to A, F and F' are described in U.S. Pat. No. 6,362,254, and are useful in forming polymer conjugates in accordance with the present invention. F and F' are spacer groups that may be the same of different. In one particular embodiment of the above, PEG is mPEG, A corresponds to —C(O)—NH—, and F and F' are both methylene or —CH$_2$—. This type of water-soluble polymer is useful for reaction with two active agents, where the two active agents are positioned at a precise or predetermined distance apart, depending upon the selection of F and F'.

In any of the representative structures provided herein, one or more degradable linkages may additionally be contained in the polymer segment, POLY, to allow generation in vivo of a conjugate having a smaller PEG chain than in the initially administered conjugate. Appropriate physiologically cleavable linkages include but are not limited to ester, carbonate ester, carbamate, sulfate, phosphate, acyloxyalkyl ether, acetal, and ketal. Such linkages when contained in a given water-soluble polymer will preferably be stable upon storage and upon initial administration.

More particularly, as described generally above, two or more water-soluble polymers connected by a hydrolyzable linkage may be represented by the following structure: PEG1-W-PEG2 (where PEG1 and PEG2 can be the same or different) and W represents a weak, hydrolyzable linkage. These water-soluble polymer structures contain PEG segments that are removable (i.e., cleavable) in vivo, as described in detail in U.S. Patent Application Publication No. 2002/0082345.

The PEG polymer used to prepare a conjugate of the invention may comprise a pendant PEG molecule having reactive groups, such as carboxyl, covalently attached along the length of the PEG rather than at the end of the PEG chain(s). The pendant reactive groups can be attached to the PEG directly or through a spacer moiety, such as an alkylene group.

Additional representative PEGs having either linear or branched structures for use in preparing the conjugates of the invention may be purchased from Nektar Therapeutics (Huntsville, Ala.). Illustrative structures are described in Nektar's 2004 Advanced PEGylation PEG reagent catalogue, the contents of which are expressly incorporated herein by reference.

Hydrolytically degradable linkages, useful not only as a degradable linkage within a polymer backbone, but preferably in the case of the instant invention, for covalently attaching a water-soluble polymer to an antimicrobial agent, include: carbonate; imine resulting, for example, from reaction of an amine and an aldehyde (see, e.g., Ouchi et al. (1997) *Polymer Preprints* 38(1):582-3); phosphate ester, formed, for example, by reacting an alcohol with a phosphate group; hydrazone, e.g., formed by reaction of a hydrazide and an aldehyde; acetal, e.g., formed by reaction of an aldehyde and an alcohol; orthoester, formed, for example, by reaction between a formate and an alcohol; and certain urethane linkages.

Additional PEG reagents for use in the invention include hydrolyzable PEGs and linkers such as those described in International Patent Application Publication No. WO 04/089280. In utilizing this approach, one or more of the free functional groups within an antimicrobial agent as described herein, e.g., amino, hydroxyl, mercapto, phosphate and/or carboxy group, is derivatized with a group sensitive to mild basic conditions, e.g., 9-fluorenylmethoxycarbonyl (Fmoc) or 2-sulfo-9-fluorenylmethoxycarbonyl (FMS), that is covalently attached to a water-soluble polymer such as a PEG. In the resulting conjugate, the antimicrobial agent and the water-soluble polymer are each covalently attached to different positions of the scaffold Fmoc or FMS structure, and are releasable under physiological conditions.

Such optional features of the polymer conjugate, i.e., the introduction of one or more degradable linkages into the polymer chain, may provide for additional control over the final desired pharmacological properties of the conjugate upon administration. For example, a large and relatively inactive conjugate (i.e., having one or more high molecular weight PEG chains attached thereto, for example, one or more PEG chains having a molecular weight greater than about 10,000, wherein the conjugate possesses essentially no or insignificant bioactivity) may be administered, which is hydrolyzed to generate a bioactive antimicrobial agent conjugate possessing a portion of the original PEG chain. Alternatively, if a degradable linkage is used to covalently attach the antimicrobial agent to the polymer, hydrolysis results in the original antimicrobial agent absent the polymer segment, or alternatively, a modified antimicrobial agent possessing a short tag portion left over from hydrolysis of the polymer segment, where the modified antimicrobial agent still retains some fraction of its antimicrobial activity. In this way, the properties of the conjugate can be more effectively tailored to balance the pharmacological properties of the conjugate upon administration.

Those of ordinary skill in the art will recognize that the foregoing discussion concerning substantially water-soluble polymers is by no means exhaustive and is merely illustrative, and that all polymeric materials having the qualities described above are contemplated. As used herein, the term "polymeric reagent" generally refers to an entire molecule, which can comprise a water-soluble polymer and a functional group.

As described above, a conjugate of the invention comprises a water-soluble polymer, POLY, covalently attached to an antimicrobial agent. Typically, for any given conjugate, there will be one to about four water-soluble polymers covalently attached to the antimicrobial agent, where the polymer may possess any of the forms described herein. In a preferred embodiment, the antimicrobial agent possesses one or two water-soluble polymers covalently attached thereto.

The particular linkage covalently attaching the antimicrobial agent to the water-soluble polymer depends on a number of factors. Such factors include, for example, the particular linkage chemistry employed, the particular antimicrobial agent, the available functional groups for covalent attachment within the antimicrobial agent, the potential presence of additional reactive functional groups within the antimicrobial agent that may optionally require protecting groups, and the like.

The conjugates of the invention can be, although are not necessarily, prodrugs, meaning that the linkage between the polymer and the antimicrobial agent is hydrolytically degradable to allow release of the antimicrobial moiety. Such linkages can be readily prepared by appropriate modification of either the peptidyl antimicrobial agent (e.g., the carboxyl group C terminus of the protein or a side chain hydroxyl group of an amino acid such as serine or threonine contained within the protein) and/or the polymeric reagent, using coupling methods commonly employed in the art combined with the teachings of the present application. Most preferred, however, are hydrolyzable linkages that are formed by reaction of a suitably activated polymer with a non-modified functional group contained within the antimicrobial agent, optionally via an intervening linker.

Alternatively, a hydrolytically stable linkage, such as an amide, urethane (also known as carbamate), amine, thioether (also known as sulfide), or urea (also known as carbamide) linkage can also be employed. One preferred hydrolytically stable linkage is an amide.

The conjugates (as opposed to an unconjugated antimicrobial agent) may or may not possess a measurable degree of activity, depending upon whether the polymer is covalently attached via a degradable or a hydrolytically stable linker. That is to say, a polymer conjugate in accordance with the invention will possesses anywhere from about 0.1% to about 100% or more of the antimicrobial activity of the unmodified parent antimicrobial agent. Preferably, conjugates possessing little or no activity contain a hydrolyzable linkage connecting the polymer to the antimicrobial agent, so that regardless of the lack of activity in the conjugate, the active antimicrobial agent (or a derivative thereof) is released upon aqueous-induced cleavage of the hydrolyzable linkage.

For conjugates possessing a hydrolytically stable linkage that couples the antimicrobial agent to the polymer, the conjugate will typically possess a measurable degree of activity. For instance, such conjugates are typically characterized as having an activity of at least about 2%, 5%, 10%, 15%, 25%, 30%, 40%, 50%, 60%, 80%, 85%, 90%, 95% 97%, 100%, or more relative to that of the unmodified parent antimicrobial agent, when measured in a suitable model, such as those well known in the art. Preferably, conjugates having a hydrolytically stable linkage (e.g., an amide linkage) will possess at least some degree of the bioactivity of the unmodified parent antimicrobial agent.

There are a number of examples of suitable water-soluble polymeric reagents useful for forming covalent linkages with reactive amino groups contained within the antimicrobial agent. Particular examples, along with the corresponding conjugate, are provided in Table 1, below. In the table, the variable (n) represents the number of repeating monomeric units and "—NH-(LY)" represents the antimicrobial agent (e.g., a lysostaphin moiety) following conjugation to the water-soluble polymer, where the "NH-" represents an amino group on the antimicrobial agent. While each polymeric portion presented in Table 1 terminates in a "CH$_3$" group, other groups (such as H, ethyl and benzyl) can be substituted therefor. Moreover, although the tables herein generally show a single water-soluble polymer attached to an antimicrobial agent, this is for illustrative purposes only. It is to be understood that a given water-soluble polymer may be covalently attached to multiple sites upon the antimicrobial agent, depending upon the reactive groups employed, synthetic strategy, size of the polymer, and so forth. For the sake of simplicity, the illustrative structures in the tables below show one water-soluble polymer covalently attached to one site on the antimicrobial agent, although such structures are meant to additionally encompass the subject polymer reagent covalently attached to more than one site.

TABLE 1

Amide-Specific Polymeric Reagents and the Antimicrobial Agent Conjugate Formed Therefrom

| Polymeric Reagent | Corresponding Conjugate |
|---|---|
| <br>mPEG-Oxycarbonylimidazole Derivative | $H_3CO-(CH_2CH_2O)_n-\overset{O}{\overset{\|}{C}}-NH-(LY)$<br>Carbamate Linkage |
| <br>mPEG Nitrophenyl Derivative | $H_3CO-(CH_2CH_2O)_n-\overset{O}{\overset{\|}{C}}-NH-(LY)$<br>Carbamate Linkage |
| 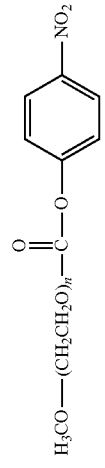<br>mPEG-Trichlorophenyl Carbonates | $H_3CO-(CH_2CH_2O)_n-\overset{O}{\overset{\|}{C}}-NH-(LY)$<br>Carbamate Linkage |
| 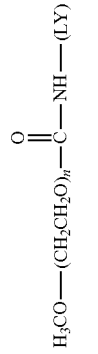<br>mPEG-Succinimidyl Derivative | $H_3C-(OCH_2CH_2)_n-O-CH_2-\overset{O}{\overset{\|}{C}}-N-(LY)$<br>Amide Linkage |
| 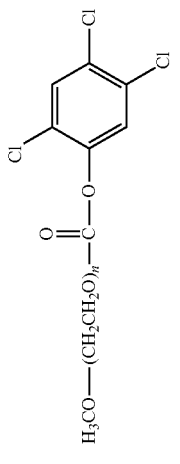<br>Homobifunctional PEG-Succinimidyl Derivative | $(LY)-NH-\overset{O}{\overset{\|}{C}}-CH_2CH_2-(OCH_2CH_2)_n-O-CH_2CH_2-\overset{O}{\overset{\|}{C}}-NH-(LY)$<br>Amide Linkages |

TABLE 1-continued

Amide-Specific Polymeric Reagents and the Antimicrobial Agent Conjugate Formed Therefrom

| Polymeric Reagent | Corresponding Conjugate |
|---|---|
| Biotin-(CH$_2$)$_4$—NH—CH$_2$CH$_2$—(OCH$_2$CH$_2$)$_n$—OCH$_2$CH$_2$C(=O)—O—N-succinimidyl<br>Heterobifunctional PEG-Succinimidyl Derivative | Biotin-(CH$_2$)$_4$—NH—CH$_2$CH$_2$—(OCH$_2$CH$_2$)$_n$—OCH$_2$CH$_2$C(=O)—NH—(LY)<br>Amide Linkage |
| H$_3$C—(OCH$_2$CH$_2$)$_n$—O—CH$_2$CH$_2$C(=O)—O—N-succinimidyl<br>mPEG-Succinimidyl Derivative | H$_3$C—(OCH$_2$CH$_2$)$_n$—O—CH$_2$CH$_2$C(=O)—NH—(LY)<br>Amide Linkage |
| H$_3$CO—(CH$_2$CH$_2$O)$_n$—CH$_2$CH$_2$NH—C(=O)—CH$_2$CH$_2$—C(=O)—O—N-succinimidyl<br>mPEG-Succinimidyl Derivative | H$_3$CO—(CH$_2$CH$_2$O)$_n$—CH$_2$CH$_2$NH—C(=O)—CH$_2$CH$_2$—C(=O)—NH—(LY)<br>Amide Linkage |
| H$_3$CO—(CH$_2$CH$_2$O)$_n$—CH$_2$CH$_2$SH—CH$_2$CH$_2$—C(=O)—O—N-succinimidyl<br>mPEG Succinimidyl Derivative | H$_3$CO—(CH$_2$CH$_2$O)$_n$—CH$_2$CH$_2$SH—CH$_2$CH$_2$—C(=O)—NH—(LY)<br>Amide Linkage |

TABLE 1-continued

Amide-Specific Polymeric Reagents and the Antimicrobial Agent Conjugate Formed Therefrom

| Polymeric Reagent | Corresponding Conjugate |
|---|---|
| $H_3C-(OCH_2CH_2)_n-O-CH_2CH_2-C(=O)-O-N$(succinimidyl)<br>mPEG-Succinimidyl Derivative | $H_3C-(OCH_2CH_2)_n-O-CH_2CH_2-C(=O)-NH-(LY)$<br>Amide Linkage |
| $H_3C-(OCH_2CH_2)_n-O-C(=O)-O-$benzotriazole<br>mPEG-Benzotriazole Carbonate Derivative | $H_3C-(OCH_2CH_2)_n-O-C(=O)-NH-(LY)$<br>Carbamate Linkage |
| $H_3C-(OCH_2CH_2)_n-NH-C(=O)-O-C_6H_4-C(=O)-O-N$(succinimidyl)<br>mPEG-Succinimidyl Derivative | $H_3C-(OCH_2CH_2)_n-NH-C(=O)-O-C_6H_4-C(=O)-NH-(LY)$<br>Carbamate Linkage |
| $H_3CO-(CH_2CH_2O)_n-C_6H_4-C(=O)-O-N$(succinimidyl)<br>mPEG-Succinimidyl Derivative | $H_3CO-(CH_2CH_2O)_n-C_6H_4-C(=O)-NH-(LY)$<br>Amide Linkage |

TABLE 1-continued

Amide-Specific Polymeric Reagents and the Antimicrobial Agent Conjugate Formed Therefrom

| Polymeric Reagent | Corresponding Conjugate |
|---|---|
| mPEG Succinimidyl Derivative | Amide Linkage |
| Branched mPEG2-N-Hydroxysuccinimide Derivative | Amide Linkage |
| Branched mPEG2-Aldehyde Derivative | Secondary Amine Linkage |
| mPEG-Succinimidyl Derivative | Amide Linkage |

TABLE 1-continued

Amide-Specific Polymeric Reagents and the Antimicrobial Agent Conjugate Formed Therefrom

| Polymeric Reagent | Corresponding Conjugate |
|---|---|
| 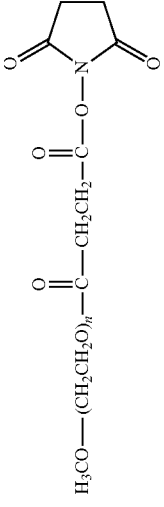 mPEG-Succinimidyl Derivative | 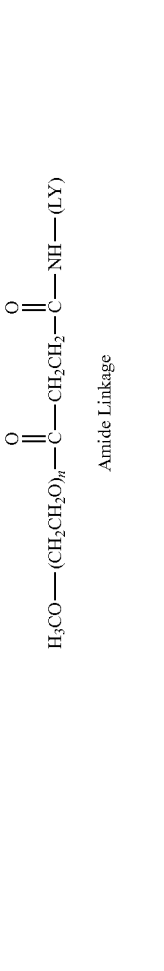 Amide Linkage |
| 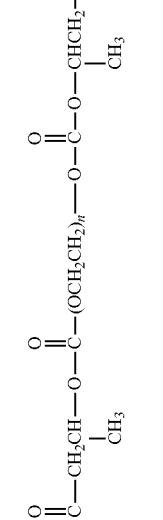 Homobifunctional PEG-Succinimidyl Derivative | 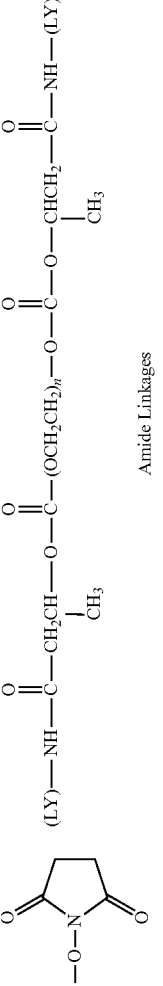 Amide Linkages |
| 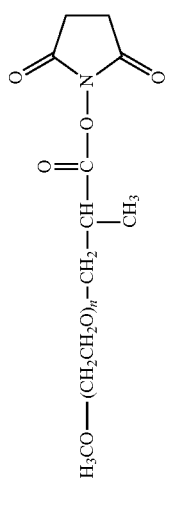 mPEG-Succinimidyl Derivative | 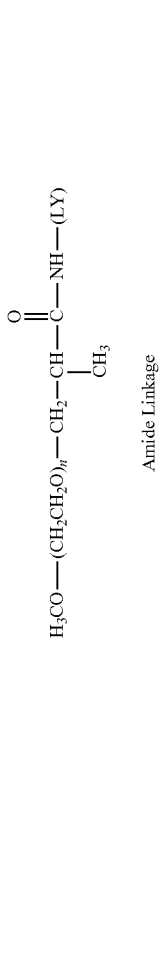 Amide Linkage |
| 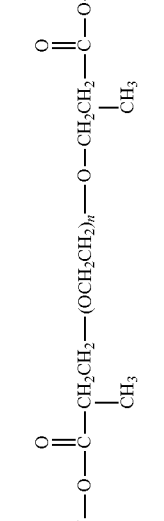 Homobifunctional PEG-Succinimidyl Propionate Derivative | 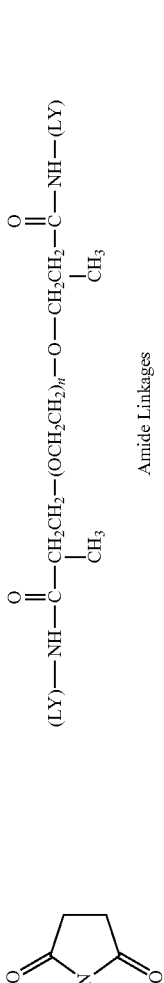 Amide Linkages |

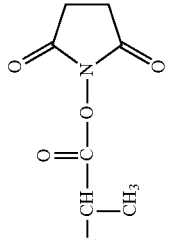

TABLE 1-continued

Amide-Specific Polymeric Reagents and the Antimicrobial Agent Conjugate Formed Therefrom

| Polymeric Reagent | Corresponding Conjugate |
|---|---|
| $H_3C-(OCH_2CH_2)_n-O-CH_2CH_2-\overset{\overset{\displaystyle O}{\|}}{C}H$ <br><br>mPEG Propionaldehyde Derivative | $H_3C-(OCH_2CH_2)_n-O-CH_2CH_2-CH_2-NH-(LY)$ <br>Secondary Amide Linkage |
| $\overset{\overset{\displaystyle O}{\|}}{H}CCH_2CH_2CH_2-(OCH_2CH_2)_n-O-CH_2CH_2CH_2-\overset{\overset{\displaystyle O}{\|}}{C}H$ <br><br>Homobifunctional PEG Butyraldehyde Derivative | $(LY)-NH-CH_2CH_2CH_2CH_2-(OCH_2CH_2)_n-O-CH_2CH_2CH_2-CH_2-NH-(LY)$ <br>Secondary Amide Linkages |
| $H_3C-(OCH_2CH_2)_n-O-CH_2CH_2CH_2-\overset{\overset{\displaystyle O}{\|}}{C}H$ <br><br>mPEG Butyraldehyde Derivative | $H_3C-(OCH_2CH_2)_n-O-CH_2CH_2CH_2-CH_2-NH-(LY)$ <br>Secondary Amide Linkage |
| $H_3C-(OCH_2CH_2)_n-O-\overset{\overset{\displaystyle O}{\|}}{C}-NH-(CH_2CH_2O)_4-CH_2CH_2CH_2-\overset{\overset{\displaystyle O}{\|}}{C}H$ <br><br>mPEG Butyraldehyde Derivative | $H_3C-(OCH_2CH_2)_n-O-\overset{\overset{\displaystyle O}{\|}}{C}-NH-(CH_2CH_2O)_4-CH_2CH_2CH_2-CH_2-NH-(LY)$ <br>Secondary Amide Linkage |
| $\overset{\overset{\displaystyle O}{\|}}{C}-(OCH_2CH_2)_n-O-\overset{\overset{\displaystyle O}{\|}}{C}-NH-(CH_2CH_2O)_4-CH_2CH_2CH_2-\overset{\overset{\displaystyle O}{\|}}{C}H$ <br>$HN-(CH_2CH_2O)_4-CH_2CH_2CH_2$ <br><br>Homobifunctional PEG Butyraldehyde Derivative | $\overset{\overset{\displaystyle O}{\|}}{C}-(OCH_2CH_2)_n-O-\overset{\overset{\displaystyle O}{\|}}{C}-NH-(CH_2CH_2O)_4-CH_2CH_2CH_2-NH-(LY)$ <br>$HN-(CH_2CH_2O)_4-CH_2CH_2CH_2-NH-(LY)$ <br>Secondary Amide Linkages |
| $H_3C-(OCH_2CH_2)_n-O-\overset{\overset{\displaystyle O}{\|}}{C}-NH-CH_2-CH_2-CH_2-CH_2$ <br>$\overset{\overset{\displaystyle O}{\|}}{C}H-\overset{\overset{\displaystyle O}{\|}}{C}-NH$ <br>$H_3C-(OCH_2CH_2)_n-O-\overset{\overset{\displaystyle O}{\|}}{C}-NH-(CH_2CH_2O)_4-CH_2CH_2CH$ <br><br>Branched mPEG2 Butyraldehyde Derivative | $H_3C-(OCH_2CH_2)_n-O-\overset{\overset{\displaystyle O}{\|}}{C}-NH-CH_2-CH_2-CH_2-CH_2$ <br>$\overset{\overset{\displaystyle O}{\|}}{C}H-\overset{\overset{\displaystyle O}{\|}}{C}-NH-(CH_2CH_2O)_4-$ <br>$H_3C-(OCH_2CH_2)_n-O-\overset{\overset{\displaystyle O}{\|}}{C}-NH-CH_2CH_2CH_2-NH-(LY)$ <br>Secondary Amide Linkage |

TABLE 1-continued

Amide-Specific Polymeric Reagents and the Antimicrobial Agent Conjugate Formed Therefrom

| Polymeric Reagent | Corresponding Conjugate |
|---|---|
| $H_3C-(OCH_2CH_2)_n-NH-\overset{O}{\underset{\|}{C}}-\overset{}{\underset{\|}{C}}H-O-CH_2$ <br> $\phantom{H_3C-(OCH_2CH_2)_n-NH-C-}HC-OCH_2-CH_2-CH_2-CH_2-\overset{O}{\underset{\|}{C}}-NH-$ <br> $H_3C-(OCH_2CH_2)_n-NH-\overset{O}{\underset{\|}{C}}-\overset{}{\underset{\|}{C}}H-O-CH_2$ <br> $-(CH_2CH_2O)_4-CH_2CH_2CH$ <br> Branched mPEG2 Butyraldehyde Derivative | $H_3C-(OCH_2CH_2)_n-NH-\overset{O}{\underset{\|}{C}}-\overset{}{\underset{\|}{C}}H-O-CH_2$ <br> $\phantom{H_3C-(OCH_2CH_2)_n-NH-C-}HC-OCH_2-CH_2-CH_2-\overset{O}{\underset{\|}{C}}-NH-$ <br> $H_3C-(OCH_2CH_2)_n-NH-\overset{O}{\underset{\|}{C}}-\overset{}{\underset{\|}{C}}H-O-CH_2$ <br> $-(CH_2CH_2O)_4-CH_2CH_2CH_2-NH-(LY)$ <br> Secondary Amide Linkage |
| $H_3C-(OCH_2CH_2)_n-O-CH_2-CH-OCH_2CH_3$ <br> $\phantom{H_3C-(OCH_2CH_2)_n-O-CH_2-CH-}\|$ <br> $\phantom{H_3C-(OCH_2CH_2)_n-O-CH_2-CH-}OCH_2CH_3$ <br> mPEG Acetyl Derivative | $H_3C-(OCH_2CH_2)_n-O-CH_2CH_2-NH-(LY)$ <br> Secondary Amide Linkage |
| mPEG Piperidone Derivative | (piperidine ring with N-C(=O)-CH₂CH₂-O-(OCH₂CH₂)ₙ-CH₃ and 4-NH-(LY)) <br> Secondary Amide Linkage <br> (to a secondary carbon) |
| $H_3C-(OCH_2CH_2)_n-O-(CH_2)_{2-5}-\overset{O}{\underset{\|}{C}}-CH_3$ <br> mPEG Methylketone Derivative | $H_3C-(OCH_2CH_2)_n-O-(CH_2)_{2-5}-\overset{NH-(LY)}{\underset{\|}{C}H}-CH_3$ <br> secondary amine linkage <br> (to a secondary carbon) |
| $H_3CO-(CH_2CH_2O)_n-\overset{O}{\underset{\|}{S}}-CH_2-CF_3$ <br> $\phantom{H_3CO-(CH_2CH_2O)_n-}\overset{\|}{O}$ <br> mPEG tresylate | $H_3CO-(CH_2CH_2O)_n-CH_2CH_2-NH-(LY)$ <br> Secondary Amide Linkage |

TABLE 1-continued

Amide-Specific Polymeric Reagents and the Antimicrobial Agent Conjugate Formed Therefrom

| Polymeric Reagent | Corresponding Conjugate |
|---|---|
| 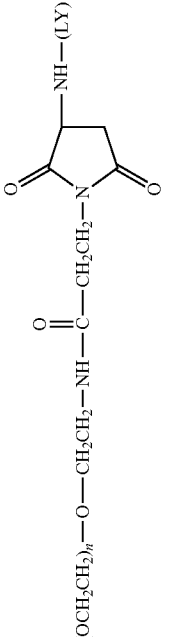 H₃C—(OCH₂CH₂)$_n$—O—CH₂CH₂—<br>mPEG Maleimide Derivative<br>(under certain reaction conditions such as pH > 8) | 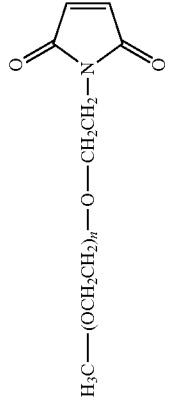 H₃C—(OCH₂CH₂)$_n$—O—CH₂CH₂—<br>Secondary Amide Linkage |
|  H₃C—(OCH₂CH₂)$_n$—O—CH₂CH₂—NH—C—CH₂CH₂—<br>mPEG Maleimide Derivative<br>(under certain reaction conditions such as pH > 8) | 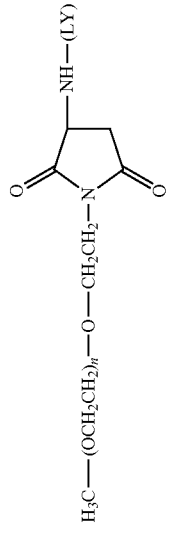 H₃C—(OCH₂CH₂)$_n$—O—CH₂CH₂—NH—C—CH₂CH₂—<br>Secondary Amide Linkage |
| 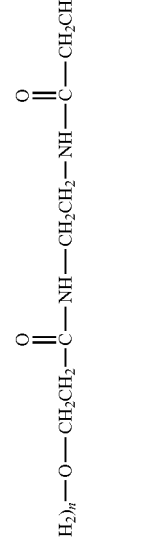 H₃C—(OCH₂CH₂)$_n$—O—CH₂CH₂—C—NH—CH₂CH₂—NH—C—CH₂CH₂—<br>mPEG Maleimide Derivative<br>(under certain reaction conditions such as pH > 8) | 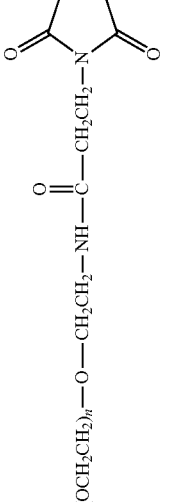 H₃C—(OCH₂CH₂)$_n$—O—CH₂CH₂—C—NH—CH₂CH₂—NH—C—CH₂CH₂—  —NH—(LY)<br>Secondary Amide Linkage |

TABLE 1-continued
Amide-Specific Polymeric Reagents and the Antimicrobial Agent Conjugate Formed Therefrom
| Polymeric Reagent | Corresponding Conjugate |
|---|---|
| 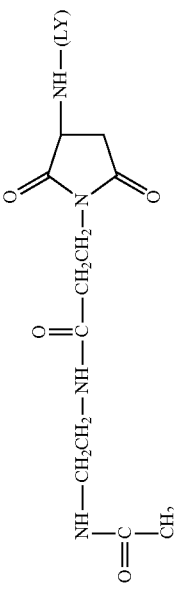 mPEG Forked Maleimide Derivative (under certain reaction conditions such as pH > 8) | 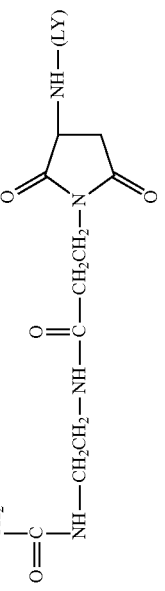 Secondary Amide Linkages |

TABLE 1-continued

Amide-Specific Polymeric Reagents and the Antimicrobial Agent Conjugate Formed Therefrom

| Polymeric Reagent | Corresponding Conjugate |
|---|---|
| Branched mPEG2 Maleimide Derivative (under certain reaction conditions such as pH > 8) | Secondary Amide Linkage |

Reaction conditions for coupling a polymeric reagent to an antimicrobial agent (such as a lysostaphin moiety) will be discussed with respect to conjugation using a polymeric reagent functionalized with a succinimidyl derivative (or other activated ester group, wherein approaches similar to those described for a succinimidyl derivative will be similar to the reaction conditions used for other activated ester group-containing polymeric reagents). Typically, conjugation of a polymeric reagent to an amino group of an antimicrobial agent is carried out at pHs from around 5 to 9.5, preferably from about 7 to about 8, at greater than 0° C. to about room temperature (such as about 4° C.) for about thirty minutes to about 24 hours, although, using different reaction conditions (e.g., a lower pH such as 6 to 7, or different) can result in the attachment of the water-soluble polymer to a different location on the antimicrobial agent. Preferred molar ratios of the polymeric reagent to protein can vary, but are typically from about 1:1 to 5:1, or even 10:1, or even up to 100:1. Increasing the pH increases the rate of reaction, while lowering the pH reduces the rate of reaction. In addition, an amide linkage can be formed reacting an amine-terminated nonpeptidic, water-soluble polymer with an antimicrobial agent bearing an activating a carboxylic acid group.

Carboxyl groups represent another functional group that can serve as a point of attachment on the antimicrobial agent (such as a lysostaphin moiety). Structurally, the conjugate will comprise the following structure:

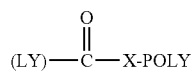

where (LY) and the adjacent carbonyl group corresponds to the carboxyl-containing antimicrobial agent, X is a linkage, preferably a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing antimicrobial agent. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Polymeric reagents containing a hydrazide moiety are also useful for conjugation at a carbonyl. To the extent that the antimicrobial agent does not contain a carbonyl moiety, a carbonyl moiety can be introduced by reducing any carboxylic acids (e.g., the C-terminal carboxylic acid) and/or by providing glycosylated or glycated (wherein the added sugars have a carbonyl moiety) versions of the antimicrobial agent. Specific examples of water-soluble derivatives containing a hydrazide moiety, along with the corresponding conjugates, are provided in Table 2, below. In addition, any water-soluble derivative containing an activated ester (e.g., a succinimidyl group) can be converted to contain a hydrazide moiety by reacting the water-soluble polymer derivative containing the activated ester with hydrazine ($NH_2$—$NH_2$) or tert-butyl carbazate [$NH_2NHCO_2C(CH_3)_3$]. In the table, the variable (n) represents the number of repeating monomeric units and "=C-(LY)" represents the residue of the antimicrobial agent (such as a lysostaphin moiety) following conjugation to the polymeric reagent. Optionally, the hydrazone linkage can be reduced using a suitable reducing agent. While each polymeric portion [e.g., $(OCH_2CH_2)_n$ or $(CH_2CH_2O)_n$] presented in Table 2 terminates in a "$CH_3$" group, other groups (such as H and benzyl) can be substituted therefor.

TABLE 2

Carboxyl-Specific Polymeric Reagents and the Antimicrobial Agent Conjugate Formed Therefrom

| Polymeric Reagent | Corresponding Conjugate |
|---|---|
| $H_3CO$—$(CH_2CH_2O)_n CH_2CH_2$—C(=O)—NH—$NH_2$<br>mPEG-Hydrazine Derivative | $H_3CO$—$(CH_2CH_2O)_n CH_2CH_2$—C(=O)—NH—N=C—(LY)<br>Hydrazone Linkage |
| $H_3CO$-$(CH_2CH_2O)_n CH_2CH_2$—O—$CH_2$—C(=O)—NH—$NH_2$<br>mPEG-Hydrazine Derivative | $H_3CO$-$(CH_2CH_2O)_n CH_2CH_2$—O—$CH_2$—C(=O)—NH—N=C—(LY)<br>Hydrazone Linkage |
| $H_3CO$—$(CH_2CH_2O)_n CH_2CH_2$—NH—C(=O)—NH—$NH_2$<br>mPEG-Hydrazine Derivative | $H_3CO$-$(CH_2CH_2O)_n CH_2CH_2$—NH—C(=O)—NH—N=C—(LY)<br>Hydrazone Linkage |

TABLE 2-continued

Carboxyl-Specific Polymeric Reagents and the Antimicrobial Agent Conjugate Formed Therefrom

| Polymeric Reagent | Corresponding Conjugate |
|---|---|
| $H_3CO-(CH_2CH_2O)_nCH_2CH_2-NH-NH-\overset{\overset{O}{\|\|}}{C}-NH-NH_2$ <br> mPEG-Hydrazine Derivative | $H_3CO-(CH_2CH_2O)_nCH_2CH_2-NH-NH-\overset{\overset{O}{\|\|}}{C}-NH-N=C-(LY)$ <br> Hydrazone Linkage |
| $H_3CO-(CH_2CH_2O)_nCH_2CH_2-NH-\overset{\overset{S}{\|\|}}{C}-NH-NH_2$ <br> mPEG-Hydrazine Derivative | $H_3CO-(CH_2CH_2O)_nCH_2CH_2-NH-\overset{\overset{S}{\|\|}}{C}-NH-N=C-(LY)$ <br> Hydrazone Linkage |
| $H_3CO-(CH_2CH_2O)_nCH_2CH_2-NH-NH-\overset{\overset{S}{\|\|}}{C}-NH-NH_2$ <br> mPEG-Hydrazine Derivative | $H_3CO-(CH_2CH_2O)_nCH_2CH_2-NH-NH-\overset{\overset{S}{\|\|}}{C}-NH-N=C-(LY)$ <br> Hydrazone Linkage |
| $H_3CO-(CH_2CH_2O)_nCH_2CH_2-NH-\overset{\overset{O}{\|\|}}{C}-NH-NH-\overset{\overset{O}{\|\|}}{C}-NH-NH_2$ <br> mPEG-Hydrazine Derivative | $H_3CO-(CH_2CH_2O)_nCH_2CH_2-NH-\overset{\overset{O}{\|\|}}{C}-NH-NH-\overset{\overset{O}{\|\|}}{C}-NH-N=C-(LY)$ <br> Hydrazone Linkage |
| $H_3CO-(CH_2CH_2O)_nCH_2CH_2-O-\overset{\overset{O}{\|\|}}{C}-NH-NH_2$ <br> mPEG-Hydrazine Derivative | $H_3CO-(CH_2CH_2O)_nCH_2CH_2-O-\overset{\overset{O}{\|\|}}{C}-NH-N=C-(LY)$ <br> Hydrazone Linkage |

Thiol groups contained within the antimicrobial agent can serve as effective sites of attachment for the water-soluble polymer. The thiol groups in such cysteine residues can then be reacted with an activated PEG that is specific for reaction with thiol groups, e.g., an N-maleimidyl polymer or other derivative, as described in U.S. Pat. No. 5,739,208 and in International Patent Publication No. WO 01/62827.

Certain antimicrobial agents such as a preprolysostaphin, prolysostaphin, lysostaphin and mature active lysostaphin lack a thiol group. In these cases, it is possible to add a cysteine residue to the antimicrobial agent using conventional synthetic techniques. See, for example, WO 90/12874. In addition, conventional genetic engineering processes can also be used to introduce a cysteine residue into the antimicrobial agent (such as a lysostaphin moiety).

Specific examples, along with the corresponding conjugate, are provided in Table 3, below. In the table, the variable (n) represents the number of repeating monomeric units and "—S-(LY)" represents the antimicrobial agent (such as a lysostaphin moiety) residue following conjugation to the water-soluble polymer. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

TABLE 3

Thiol-Specific Polymeric Reagents and the Antimicrobial Agent Moiety Conjugate Formed Therefrom

| Polymeric Reagent | Corresponding Conjugate |
|---|---|
| $H_3C-(OCH_2CH_2)_n-O-CH_2CH_2-$ [maleimide] <br> mPEG Maleimide Derivative | $H_3C-(OCH_2CH_2)_n-O-CH_2CH_2-$ [succinimide]$-S-(LY)$ <br> Thioether Linkage |
| $H_3CO-(CH_2CH_2O)_n-CH_2CH_2-$ [maleimide] <br> mPEG Maleimide Derivative | $H_3CO-(CH_2CH_2O)_n-CH_2CH_2-$ [succinimide]$-S-(LY)$ <br> Thioether Linkage |
| $H_3CO-(CH_2CH_2O)_n-C(=O)-NH-CH_2CH_2OCH_2CH_2OCH_2CH_2NH-C(=O)-CH_2CH_2-$ [maleimide] <br> mPEG Maleimide Derivative | $H_3CO-(CH_2CH_2O)_n-C(=O)-NH-CH_2CH_2OCH_2CH_2OCH_2CH_2NH-C(=O)-CH_2CH_2-$ [succinimide]$-S-(LY)$ <br> Thioether Link TABLE 3-continued Thiol-Specific Polymeric Reagents and the Antimicrobial Agent Moiety Conjugate Formed Therefrom

| Polymeric Reagent | Corresponding Conjugate |
|---|---|

(Table contents are chemical structure diagrams showing mPEG Maleimide Derivatives and mPEG Forked Maleimide Derivative reagents paired with their corresponding Thioether Linkage conjugates.)

TABLE 3-continued

Thiol-Specific Polymeric Reagents and the Antimicrobial Agent Moiety Conjugate Formed Therefrom

| Polymeric Reagent | Corresponding Conjugate |
|---|---|
| branched mPEG2 Maleimide Derivative | Thioether Linkage |
| branched mPEG2 Maleimide Derivative | Thioether Linkage |

TABLE 3-continued

Thiol-Specific Polymeric Reagents and the Antimicrobial Agent Moiety Conjugate Formed Therefrom

| Polymeric Reagent | Corresponding Conjugate |
|---|---|
| Branched mPEG2 Forked Maleimide Derivative | Thioether Linkages |

TABLE 3-continued

Thiol-Specific Polymeric Reagents and the Antimicrobial Agent Moiety Conjugate Formed Therefrom

| Polymeric Reagent | Corresponding Conjugate |
|---|---|
| $H_3C-(OCH_2CH_2)_n-NH-C(=O)-O-CH_2-$ <br> $\quad\quad\quad\quad\quad\quad\quad\quad\quad\quad\quad\quad HC-$ <br> $H_3C-(OCH_2CH_2)_n-NH-C(=O)-O-CH_2-$ | $H_3C-(OCH_2CH_2)_n-NH-C(=O)-O-CH_2-$ <br> $\quad\quad\quad\quad\quad\quad\quad\quad\quad\quad\quad\quad HC-$ <br> $H_3C-(OCH_2CH_2)_n-NH-C(=O)-O-CH_2-$ |
| Maleimide-linked branched mPEG2 structure with $-NH-CH_2CH_2-NH-C(=O)-CH_2CH_2-N$(maleimide) arms <br><br> Branched mPEG2 Forked Maleimide Derivative | Succinimide-S-(LY) conjugate with same branched structure <br><br> *Corresponding Conjugate* |
| $H_3C-(OCH_2CH_2)_n-O-CH_2CH_2-S(=O)_2-CH=CH_2$ <br><br> mPEG Vinyl Sulfone Derivative | $H_3C-(OCH_2CH_2)_n-O-CH_2CH_2-S(=O)_2-CH_2-CH_2-S-(LY)$ <br><br> Thioether Linkages |
| | $H_3C-(OCH_2CH_2)_n-O-CH_2CH_2-S(=O)_2-CH_2-CH_2-S-(LY)$ <br><br> Thioether Linkage |
| $H_3C-(OCH_2CH_2)_n-O-CH_2CH_2-C(=O)-NH-CH_2-CH_2-SH$ <br><br> mPEG Thiol Derivative | $H_3C-(OCH_2CH_2)_n-O-CH_2CH_2-C(=O)-NH-CH_2-CH_2-S-S-(LY)$ <br><br> Disulfide Linkage |

TABLE 3-continued

Thiol-Specific Polymeric Reagents and the Antimicrobial Agent Moiety Conjugate Formed Therefrom

| Polymeric Reagent | Corresponding Conjugate |
|---|---|
| HS—CH$_2$CH$_2$—NH—C(=O)—CH$_2$CH$_2$—(OCH$_2$CH$_2$)$_n$—C(=O)—NH—CH$_2$—CH$_2$—SH  Homobifunctional PEG Thiol Derivative | (LY)-S—S—CH$_2$CH$_2$-NH—C(=O)—CH$_2$CH$_2$—(OCH$_2$CH$_2$)$_n$-(OCH$_2$CH$_2$)$_n$—C(=O)—NH—CH$_2$—CH$_2$—S—S—(LY)  Disulfide Linkages |
| H$_3$CO—(CH$_2$CH$_2$O)$_n$—CH$_2$CH$_2$CH$_2$—S—S—[pyridine]  mPEG Disulfide Derivative  As described in copending U.S. Provisional Application No. 60/639,823 filed on Dec. 21, 2004 and entitled "Stabilized Polymeric Thiol Reagents." | H$_3$CO—(CH$_2$CH$_2$O)$_n$—CH$_2$CH$_2$CH$_2$—S—S—(LY)  Disulfide Linkage |
| [pyridine]—S—S—CH$_2$CH$_2$—(CH$_2$CH$_2$O)$_n$—CH$_2$CH$_2$CH$_2$—S—S—[pyridine]  Homobifunctional Disulfide Derivative  As described in copending U.S. Provisional Application No. 60/639,823 filed on Dec. 21, 2004 and entitled "Stabilized Polymeric Thiol Reagents." | (LY)-S—S—CH$_2$CH$_2$—(CH$_2$CH$_2$O)$_n$—CH$_2$CH$_2$CH$_2$—S—S—(LY)  Disulfide Linkages |

With respect to conjugates formed from water-soluble polymers bearing one or more maleimide functional groups (regardless of whether the maleimide reacts with an amine or thiol group on the antimicrobial agent moiety), the corresponding maleamic acid form(s) of the water-soluble polymer can also react with the antimicrobial agent. Under certain conditions (e.g., a pH of about 7-9 and in the presence of water), the maleimide ring will "open" to form the corresponding maleamic acid. The maleamic acid, in turn, can react with an amine or thiol group of an antimicrobial agent. Exemplary maleamic acid-based reactions are schematically shown below. POLY represents the water-soluble polymer, and (LY) represents the antimicrobial agent (such as a lysostaphin moiety).

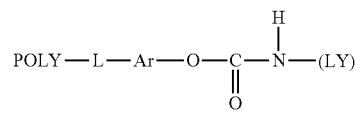

where POLY is a water-soluble polymer as described herein, L is a linking group, Ar is an aromatic group, and —NH-(LY) taken together represents an antimicrobial agent (such as a lysostaphin moiety) having an amino group. This particular structure possesses a hydrolyzable carbamate bond, such that the antimicrobial agent is released upon hydrolysis. Preferably, upon hydrolysis, the parent antimicrobial agent is released, along with $CO_2$ and the corresponding aromatic alcohol. Preferred aromatic groups are ortho, meta, or para-substituted phenyl. Preferred L groups for this particular embodiment of the invention are —O— and —NH—C(O)—. Also encompassed by the above are dumbbell-type structures having an antimicrobial agent (such as a lysostaphin moiety) or attached via an identical linkage to the POLY terminus. Particular polymers and conjugates falling within the above generalized structure are described in U.S. Pat. No. 6,413,507, the contents of which are incorporated herein by reference.

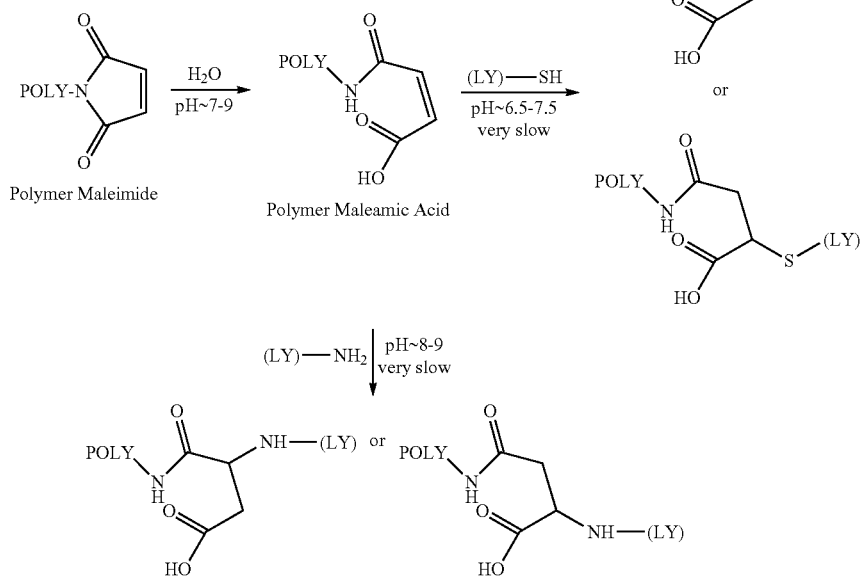

A representative conjugate in accordance with the invention can have the following structure:

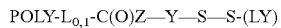

POLY-$L_{0,1}$-C(O)Z—Y—S—S-(LY)

wherein POLY is a water-soluble polymer, L is an optional linker, Z is a heteroatom selected from the group consisting of O, NH, and S, and Y is selected from the group consisting of $C_{2-10}$ alkyl, $C_{2-10}$ substituted alkyl, aryl, and substituted aryl, and (LY) is an antimicrobial agent (such as a lysostaphin moiety). Polymeric reagents that can be reacted with an antimicrobial agent moiety and result in this type of conjugate are described in U.S. Patent Application Publication No. 2005/0014903.

With respect to polymeric reagents, those described here and elsewhere can be purchased from commercial sources (e.g., Nektar Therapeutics, Huntsville, Ala.). In addition, methods for preparing the polymeric reagents are described in the literature.

In some instances, the conjugates provided herein will comprise a degradable linkage. An exemplary conjugate comprising a degradable linkage will have the following structure:

In those instances where the antimicrobial agent contains many amino groups, it may be desirable to block one or more amino groups, thereby resulting in fewer multi-conjugated species. For example, the antimicrobial agents preprolysostaphin, prelysostaphin, lysostaphin and mature active lysostaphin each have several amine-containing lysine residues that could potentially result in highly conjugates species. In view thereof, one may either employ a protection/deprotection strategy as is commonly known in the art, or alternatively, employ separation/purification techniques to isolate a desired conjugate or type of conjugate resulting from a random PEGylation approach (e.g., mono-PEG mers, di-PEG mers, tri-PEG mers, etc.).

Typically, although not necessarily, the linkage between the antimicrobial agent (such as a lysostaphin moiety) and the polymeric reagent includes one or more atoms such as one or more of carbon, nitrogen, sulfur, and combinations thereof. For instance, preferred hydrolytically stable linkages comprise an amide, secondary amine, carbamate, thioether, or disulfide group. Optionally, additional atoms can connect the linkage to the chain of repeating monomers within the polymeric reagent. The same holds true for embodiments wherein the linkage is degradable, i.e., comprises a hydrolytically degradable moiety. Typically, the degradable linkage, when considered overall, contains additional atoms or combinations of atoms connecting the degradable moiety per se to the polymer and/or the antimicrobial agent. Nonlimiting examples of specific series of atoms connecting the antimicrobial agent to the chain of repeating monomers designated herein as POLY include those selected from the group consisting of —O—, —S—, —S—S—, —C(O)—, —O—C(O)—, —C(O)—O—, —C(O)—NH—, —NH—C(O)—NH—, —O—C(O)—NH—, —C(S)—, —CH$_2$—, —CH$_2$CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—CH$_2$—O—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—CH$_2$—CH$_2$—, —CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, and —O—C(O)—CH$_2$—CH$_2$—CH$_2$—. Additionally, bifunctional linkers such as amino acids or difunctional PEG oligomers may be used to connect the antimicrobial agent to the polymeric reagent.

In one or more embodiments of the invention, the conjugates can be in the form of a multi-armed conjugate. Multi-armed polymeric reagents for use in forming conjugates having multiple antimicrobial agents covalently attached thereto have been described previously herein. Multi-armed conjugates are particularly attractive in cases where high doses of the antimicrobial agent are required to deliver therapeutically effective amounts of the agent. In this way, the antimicrobial agent is "loaded up", preferably releasably, onto a single polymer molecule having several reactive sites suitable for covalent attachment.

One preferred type of multi-armed polymer for achieving maximal antimicrobial agent loading is a multi-arm block copolymer having an inner core region defined by a central core molecule having polypeptide segments covalently attached thereto and an outer hydrophilic region defined by hydrophilic polymer segments covalently attached to each of the polypeptide polymer segments. Thus, each arm of the multi-arm structure is a block copolymer comprising an inner (i.e., closer or proximal to the central core molecule) polypeptide polymer segment and an outer (i.e., further or distal from the central core molecule) hydrophilic polymer segment. Such multi-arm block copolymers are particularly well suited for encapsulation or entrapment of biologically active molecules within the inner core region. As used in the present context, "encapsulation" or "entrapment" is intended to refer to the physical confinement of an antimicrobial agent within the inner core region of the copolymer, whether by covalent attachment, charge interaction, metal-acid complex, van der Waals forces, or other attraction or bonding force. Such unimolecular multi-arm block copolymers typically have a total number average molecular weight of from about 5,000 Da to about 120,000 Da, preferably from about 10,000 Da to about 100,000 Da, and more preferably from about 20,000 Da to about 80,000 Da.

The outer hydrophilic polymer segments are preferably poly(ethylene glycol), although other hydrophilic polymer segments can also be used. The use of a polypeptide polymer segment as part of the inner core region of the unimolecular multi-arm structure provides tremendous flexibility in designing and adjusting the drug delivery properties of the multi-arm structure. Interaction between an antimicrobial agent and the core region of the unimolecular multi-arm structure can greatly affect drug loading and drug release characteristics. In the present invention, depending on the structure of the polypeptide polymer segments, the inner core region can be hydrophobic, charged, suitable for covalent attachment to drug molecules, or any combination thereof.

Preferably, the central core molecule is a residue of a polyamine having at least three termini bearing an amine group. The use of a polyamine core is preferred because the amine groups of the core readily react with the carboxylic acid group of an amino acid to form an amide linkage. Core molecules having other functional groups available for attachment to the copolymer arms can, however, also be used. In embodiments utilizing a polyamine core, the number of amine groups will dictate the number of copolymer arms in the multi-arm structure. Preferably, the polyamine comprises from 3 to about 25 amine groups. In various embodiments, the polyamine comprises at least about 5 amine groups, at least about 8 amine groups, or at least about 10 amine groups. Multi-armed polymers having these types of structures are described in detail in International Patent Application Publication No. WO/04060977.

Illustrative polymer structures include multi-arm (3, 4, 5, 6, 7, 8, 9, 10, 11 or 12-arm) poly(benzyl aspartate)-PEG, poly (aspartic acid)-PEG having multiple antimicrobial agents covalently attached to the polypeptide core of the structure, preferably although not necessarily via degradable linkages such as ester and hydrolyzable carbamate. Alternatively, rather than being covalently attached, an antimicrobial agent may be entrapped within the inner core region.

An illustrative schematic showing covalent attachment of a particular hydroxyl group of an antimicrobial agent to a multi-armed polymer is provided below. Selective attachment of a polymer at one hydroxy site within the antimicrobial agent is achieved via a spacer molecule having at its terminus, a reactive group such as an amine.

In contrast to the conjugates previously described, additionally provided herein are hydrogel-antimicrobial agent compositions where the antimicrobial agent is not necessarily covalently attached to the polymer component(s), which are present in the form of a gel. Such hydrogels can be crosslinked or non-cross-linked, and preferably contain a PEG-component. In one particular embodiment, the hydrogel components are non-cross-linked or are lightly crosslinked to facilitate release of the antimicrobial agent. The antimicrobial agent may be present in conjugated and/or unconjugated form.

An illustrative hydrogel possesses the aromatic-hydrolyzable carbamate segment described previously above. In particular, the hydrogel is composed of a polymer bonded to a crosslinking agent through a hydrolyzable carbamate linkage. The crosslinking agent in a preferred embodiment is a difunctional polymer as described above having the formula:

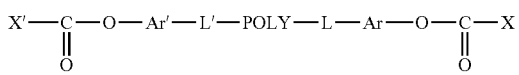

wherein POLY, POLY', L, L', X, X', Ar, and Ar' are as described previously.

In a preferred embodiment, the crosslinking agent has the formula:

wherein X and L are as described above. Thus, the crosslinking of a polymer having multiple amino groups with the above crosslinking agent is illustrated below:

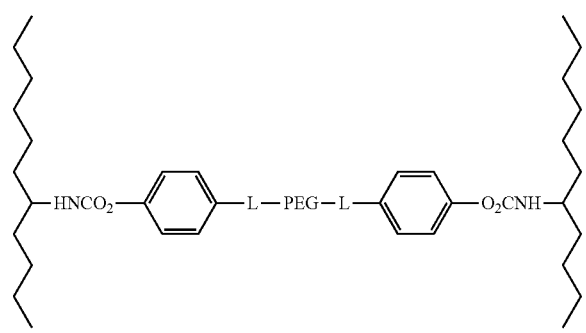

where the zig-zag notation represents a polymer having amine groups and where L is as described above. The carbamate linkages between the polymer portions and the crosslinker are hydrolyzable. Thus, this hydrogel gradually breaks down or degrades in the body as a result of the hydrolysis of the carbamate linkages.

Another type of advantageous hydrogel for preparing a sustained delivery antimicrobial agent composition possesses carbonate linkages. More particularly, provided is a water soluble, nonpeptidic polymer composed of two or more oligomers linked together by hydrolytically degradable carbonate linkages, as described U.S. Pat. No. 6,348,558, the contents of which is expressly incorporated herein by reference. The polymer can be hydrolytically degraded into small oligomers in an aqueous environment, e.g., in vivo, and can be used to prepare degradable hydrogels.

A representative polymer of this sort is represented by the formula: $X-O-[(-CH_2CH_2-O-)_n-CO_2-]_m-(CH_2CH_2O)_n-Y$, where n is an integer of from about 2 to about 2,000, m is an integer of from about 2 to about 200, and where X and Y each independently is H, alkyl, alkenyl, aryl, or a reactive moiety, and can be same or different. In the instance where either X or Y (or both) is reactive with a functional group of the antimicrobial agent, then the antimicrobial agent may optionally be covalently attached thereto in yet another embodiment of the invention.

In yet another embodiment, a hydrogel for use in preparing an antimicrobial agent composition is a thiosulfonate gel. In accordance with this embodiment of the invention, hydrogel-forming components are preferably multi-arm thiosulfonate polymer derivatives that form a crosslinked polymer composition when exposed to base, without requiring the presence of a second cross-linking reagent, redox catalyst, or radiation. Such thiosulfonate polymer derivatives can also form a hydrogel by reaction with a water-soluble polymer having at least two thiol groups.

Generally, such compositions comprise hydrogel-forming components corresponding to the formula below:

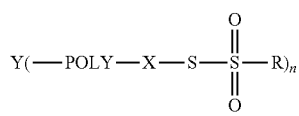

where POLY is a water-soluble polymer, n ranges from 3 to about 100, X is a linking group, Y is a moiety derived from a molecule having at least three nucleophilic groups, and R is an alkyl or aryl group. Exemplary linking groups are described elsewhere. The water-soluble polymer may optionally contain at least one degradable linkage, e.g., an ester, carbonate, acetal, orthoester, phosphate, or thiolester. The presence of one or more degradable linkages allows for the degradation of the polymer chains (e.g., by hydrolysis or enzymatic degradation) with concomitant breakdown and dissolution of the hydrogel. In a preferred embodiment, particularly when the antimicrobial agent is a lysostaphin moiety, the hydrogel- or polymer-containing composition effective to form a hydrogel, is one which does not exhibit reverse gelation properties, i.e., exists as a liquid below physiological temperature but which forms a hydrogel at physiological temperature. As an example, such hydrogel or hydrogel forming compositions will typically be made of polymers other than Poloxomer 407™.

Hydrogel compositions of the invention can be prepared prior to use. Formed hydrogel compositions may optionally be subject to dehydration or lyophilization in order to remove bound water and used as either the intact hydrogel or reduced to powder or particulate form. Hydrogel compositions of the invention may also be employed without dehydration or lyophilization as formed objects or maybe incorporated into delivery systems including without limitation: ocular insert, suppositories, pessaries, transdermal patches, or capsules filled with the hydrogel compositions.

Regardless of the form of the hydrogel-forming composition or hydrogel composition, it is possible to package the compositions in single use, multiple use or bulk containers. The preparations may optionally be sterilized by art-recognized procedures. In one preferred embodiment, the materials are packaged in sterile single use containers. In other embodiments, the materials are packaged for ease of reconstitution by addition of water, aqueous solutions or suspensions in single or multiple use containers. In another embodiment, the materials are sold as a kit with a base to initiate gel formation.

Having described various conjugates and hydrogels, purification—with particular regard to conjugates—will now be discussed. As pointed out above, the conjugates of the invention can be purified to obtain/isolate different conjugated species. Specifically, the reaction mixture can be purified to obtain an average of anywhere from one, two, or three or even more PEGs per antimicrobial agent. Preferred are conjugates having one polymer molecule attached thereto. The strategy for purification of the final conjugate reaction mixture will depend upon a number of factors, including, for example, the molecular weight of the polymeric reagent employed, the particular antimicrobial agent, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-antimicrobial agent ratios (e.g., 1-mer, 2-mer, 3-mer, and so forth, wherein "1-mer" indicates one polymer to an antimicrobial agent, "2-mer" indicates two polymers attached to an antimicrobial agent, and so on) on the basis of their differing molecular weights (where the difference corresponds essentially to the average molecular weight of the water-soluble polymer portion). For example, in an exemplary reaction where a 60,000 Dalton polypeptide is randomly conjugated to a polymeric reagent having a molecular weight of about 20,000 Daltons, the resulting reaction mixture may contain unmodified protein (having a molecular weight of about 20,000 Daltons), monoPEGylated protein (having a molecular weight of about 80,000 Daltons), diPEGylated protein (having a molecular weight of about 140,000 Daltons), and so forth.

While this approach can be used to separate PEG and polymer-antimicrobial agent conjugates having different molecular weights, this approach is generally ineffective for separating positional isomers having different polymer attachment sites within the antimicrobial agent. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) or other functional groups of the antimicrobial agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) *Anal. Biochem,* 107:60-63), and (iv) sodium dodecyl sulfate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

The resulting purified compositions are preferably substantially free of proteins that do not have antimicrobial activity. In addition, the compositions preferably are substantially free of all other non-covalently attached water-soluble polymers.

The antimicrobial activity of the conjugates and compositions of the invention may be determined using a suitable in vivo or in vitro model, depending upon the known activity of the particular antimicrobial agent employed. For example, U.S. Patent Application Publication No. 2003/0215436 describes a method for assessing the in vivo activity of lysostaphin conjugates. As described therein, it is possible to measure the drop in absorbance at 650 nm of a solution containing heat-killed SA5 (HKSA5). This method can be used to measure the activity of other lysostaphin moiety conjugates as well. Furthermore, if necessary, this method can be used to measure the activity of any proposed lysostaphin moiety.

The conjugates are typically part of a composition. The composition may contain a single type of polymer conjugate, e.g., solely PEG-antimicrobial agent monomers (i.e., having only one PEG chain covalently attached to the antimicrobial agent, although the PEGs may be covalently attached to different positions within the antimicrobial agent, e.g., at different amino acids within the sequence), or may contain a plurality of conjugates, preferably although not necessarily, each having from about one to about three water-soluble polymers covalently attached to one antimicrobial agent.

With respect to the conjugates in the composition, the composition will satisfy one or more of the following characteristics: at least about 85% of the conjugates in the composition will have from one to four polymers attached to the antimicrobial agent; at least about 85% of the conjugates in the composition will have from one to three polymers attached to the antimicrobial agent; at least about 85% of the conjugates in the composition will have from one to two polymers attached to the antimicrobial agent; at least about 85% of the conjugates in the composition will have one polymer attached to the antimicrobial agent; at least about 95% of the conjugates in the composition will have from one to four polymers attached to the antimicrobial agent; at least about 95% of the conjugates in the composition will have from one to three polymers attached to the antimicrobial agent; at least about 95% of the conjugates in the composition will have from one to two polymers attached to the antimicrobial agent; at least about 95% of the conjugates in the composition will have one polymer attached to the antimicrobial agent; at least about 99% of the conjugates in the composition will have from one to four polymers attached to the antimicrobial agent; at least about 99% of the conjugates in the composition will have from one to three polymers attached to the antimicrobial agent; at least about 99% of the conjugates in the composition will have from one to two polymers attached to the antimicrobial agent; and at least about 99% of the conjugates in the composition will have one polymer attached to the antimicrobial agent.

As discussed above, control of the desired number of polymers for any given antimicrobial agent can be achieved by selecting the proper polymeric reagent, the ratio of polymeric reagent to antimicrobial agent, temperature, pH conditions, and other aspects of the conjugation reaction. In addition, reduction or elimination of the undesired conjugates (e.g., those conjugates having four or more attached polymers) can be achieved by purification.

Optionally, the compositions of the invention may further comprise one or more pharmaceutically acceptable excipients to provide a pharmaceutical composition. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerin, vegetable oils, phospholipids, and surfactants.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for use in the composition include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the antimicrobial agent and the polymeric reagent) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate or composition in order to determine which amount produces a clinically desired endpoint (e.g. reduction in bacterial load).

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. If desired, the conjugates as well as the compositions comprising the conjugates can be frozen or freeze dried for long term storage.

Preferably, the compositions described herein are in unit dosage form, meaning an amount of a conjugate or composition of the invention appropriate for a single dose, in a pre-measured or pre-packaged form.

The compositions of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical composition). As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of a conjugate described herein. Those of ordinary skill in the art appreciate which conditions a specific conjugate can effectively treat. For example, the conjugates can be used to treat individuals infected with a staphylococcal infection. The actual dose to be administered will vary depend upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. Generally, a therapeutically effective amount will range from about 0.001 mg to 300 mg per dose, repeated as necessary.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred conjugate and compositions are those requiring dosing less frequently than once a day. That is to say, preferably, the composition of the invention is administered twice daily, once daily, once every other day, twice a week, once a week, once every two weeks, or once a month. Even more preferred are conjugates and compositions that are administered no more frequently than once a week, even more preferably no more frequently than twice monthly (every two weeks).

One advantage of administering certain conjugates of the present invention is that individual water-soluble polymer portions including the entire polymer can be cleaved off Such a result is advantageous when clearance from the body is potentially a problem because of the polymer size. Optimally, cleavage of each water-soluble polymer portion is facilitated through the use of physiologically cleavable and/or enzymatically degradable linkages such as urethane, carbonate or ester-containing linkages. In this way, clearance of the conjugate (via cleavage of individual water-soluble polymer portions) can be modulated by selecting the polymer molecular size and the type functional group that provides the desired clearance properties. One of ordinary skill in the art can determine the optimal molecular size of the polymer as well as the cleavable functional group. For example, one can determine a preferred polymer molecular size, structure, and/or cleavable functional group by preparing a variety of polymer derivatives with different polymer weights and cleavable functional groups, and then conducting in-vitro or in vivo assays as described herein to assess efficacy. Alternatively, clearance profiles may be obtained (e.g., through periodic blood or urine sampling) using suitable in-vivo models.

The conjugates and compositions of the invention may be co-administered with one or more additional antimicrobial agents.

It is to be understood that while the invention has been described in conjunction with preferred specific embodiments, the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

All chemical reagents referred to in the appended examples are commercially available or can be prepared based on information available in the art unless otherwise indicated.

All PEG reagents referred to in the appended examples are available from Nektar, Huntsville, Ala., unless otherwise indicated. All $^1$H NMR data was generated by a 300 or 400 MHz NMR spectrometer manufactured by Bruker.

To prepare the stock solution, lysostaphin was dissolved in 50 mM sodium phosphate buffer, pH 6.9, to provide a concentration of 2.3 mg/mL.

All HPLC data was generated on an Agilent 1100 HPLC with UV/VIS detection using reverse phase chromatography. A PRP-3, C3, 4.1×50 mm column (Hamilton, cat. 79807) was used with mobile phase A=0.1% trifluoracetic acid and mobile phase B=0.1% trifluoroacetic acid in acetonitrile. The flow rate was 0.5 mL/min, and the samples were detected at 220 nm.

All MALDI-TOF data was generated on an Omniflex, benchtop instrument manufactured by Bruker Daltonics.

Sodium dodecyl sulfate-polyacrylamide gel electrophoresis (SDS-PAGE) was used in conjunction with a gel documentation system (KODAK Gel Logic 200) to analyze the PEG-protein conjugates. The samples were loaded onto 4-12% Bis-Tris precast gels from Invitrogen. The samples were run on an XCell SureLock™ Mini-Cell 30 from Invitrogen for 30 min at 200V using 1×MES SDS electrophoresis buffer (Invitrogen). The gels were stained with GelCode blue for one-two hours and destained prior to imaging.

Example 1

PEGylation of Lysostaphin with mPEG SBC at pH 6.95

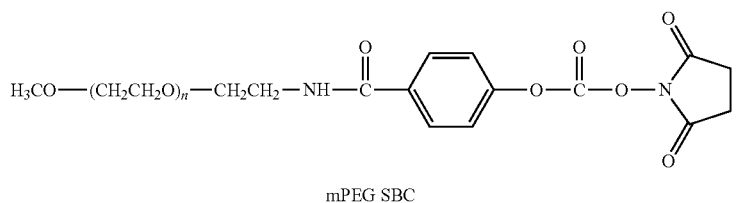

mPEG SBC

The degradable PEG reagent, mPEG SBC having a weight average molecular weight of 5,000 Daltons, was warmed from −20° C. to room temperature in a dessicator. A 5.15 mL aliquot of lysostaphin was removed from the stock solution (2.33 mg/mL in a 50 mM sodium phosphate buffer, pH 6.95). mPEG SBC (12.6 mg) was measured and quickly dissolved in 126 μL 2 mM HCl to form an mPEG SBC solution. The mPEG SBC solution (111.4 μL) was quickly added to lysostaphin. The molar ratio of mPEG SBC to protein was 5:1. After the mPEG SBC solution was added, the pH was 7.1. The reaction proceeded at room temperature for 0.5 hours on a Rotomix (slow speed, Thermolyne) and was then quenched by the addition of 4 μL at acetic acid to lower the pH to pH 5.2+/−0.2. A composition comprising a degradable conjugate of mPEG$_{5,000\ Da}$-lysostaphin (Conjugate A$_{5k,\ pH\ 6.95}$) was formed. A structural representation of the 1-mer version of the mPEG$_{5,000\ Da}$-lysostaphin (Conjugate A$_{5k,\ pH\ 6.95}$) prepared in accordance with this example is provided below (wherein "—NH-LY" represents a residue of lysostaphin).

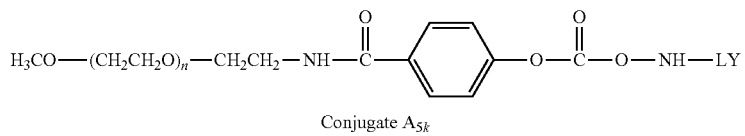

Conjugate A$_{5k}$

In order to purify the composition comprising mPEG$_{5,000\ Da}$-lysostaphin (Conjugate A$_{5k,\ pH\ 6.95}$), a HiTrap SP HP Sepharose cation exchange column (5 mL, Amersham Biosciences, cat. 17-1152-01, lot #298974) was used with an FPLC (Pharmacia). The start buffer was 25 mM sodium acetate, pH 5.3, and the elution buffer was 25 mM HAc/NaAc with 500 mM NaCl, pH 5.3. The flow rate was 3 mL/min, and the sample loading range was 2.33 to 5 mg lysostaphin. Table 4 presents a summary of the purification gradients used.

TABLE 4

Purification Methods for mPEG$_{5,000\ Da}$-Lysostaphin (Conjugate A$_{5k,\ pH\ 6.95}$)

| Volume (ml) | % B |
|---|---|
| 0 | 0 |
| 25 | 0 |
| 35 | 33 |
| 95 | 33 |

TABLE 4-continued

Purification Methods for mPEG$_{5,000\ Da}$-Lysostaphin (Conjugate A$_{5k,\ pH\ 6.95}$)

| Volume (ml) | % B |
|---|---|
| 105 | 37 |
| 145 | 37 |
| 150 | 100 |
| 165 | 100 |
| 175 | 0 |
| 225 | 0 |

Because there was not complete separation of the native ("unconjugated") lysostaphin, improvement of the purification is warranted (although there may be certain circumstances wherein a composition comprising mixtures of conjugated and unconjugated lysostaphin might be desirable). Many 1-mer fractions had to be cut because of high native content leading to a product that has a higher 2-mer percentage in order to minimize native contamination of the conjugate.

Figure 2:
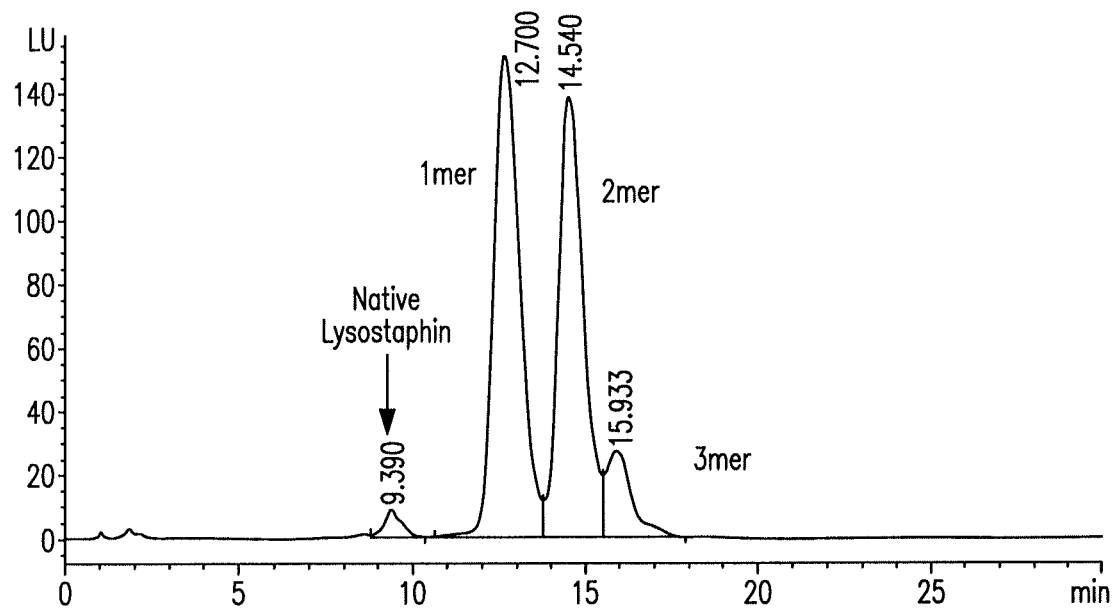
FIG. 2 corresponds to the results of a reverse phase HPLC analysis of a mPEG$_{5,000\ Da}$-lysostaphin product, as described in Example 1.
Figure 3:
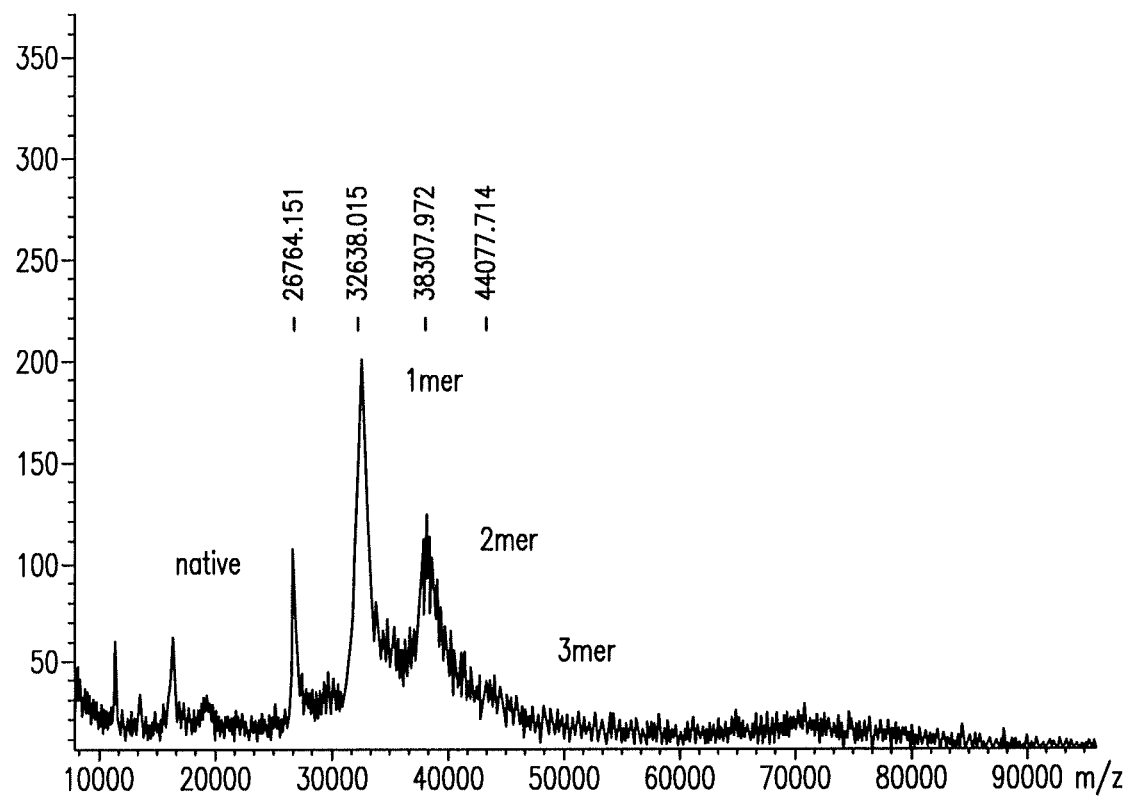
FIG. 3 corresponds to the results of MALDI-TOF analysis of a mPEG$_{5,000\ Da}$-lysostaphin product, as described in Example 1.

The now purified mPEG$_{5,000\ Da}$-lysostaphin (Conjugate A$_{5k,\ pH\ 6.95}$) produced from the PEGylation of lysostaphin with mPEG SBC at pH 6.95 was characterized and quantified. According to reverse phase chromatography, the PEGylation reaction yield of mono-PEGylated conjugate (the "1-mer") is ~44.7% (results shown in FIG. 1). The final purified product, which contains a mixture of mono- and di-PEG conjugates, was analyzed by reverse phase HPLC (results shown in FIG. 2) and MALDI-TOF (results shown in FIG. 3).

Concentration and Buffer Exchange. A YM3 ultrafiltration membrane was equilibrated in milli-Q water for one hour with three exchanges of water. It was then mounted in an ultrafiltration unit (50 mL stirred cell, model 8050, Amicon). The purified mPEG$_{5,000\ Da}$-lysostaphin (Conjugate A$_{5k,\ pH\ 6.95}$) 1-mer solution was transferred into the unit. The ultrafiltration unit was capped and connected to the N$_2$ gas line at a pressure of 55 psi. The purified solution was concentrated over a two day period until the volume was reduced.

The conjugate remained in the purification buffer at pH 5.3 due to the instability of the degradable conjugate at higher pH. The product concentration was determined by UV spectroscopy. The final concentration of the protein conjugate was 1.1 mg/mL.

Figure 4:
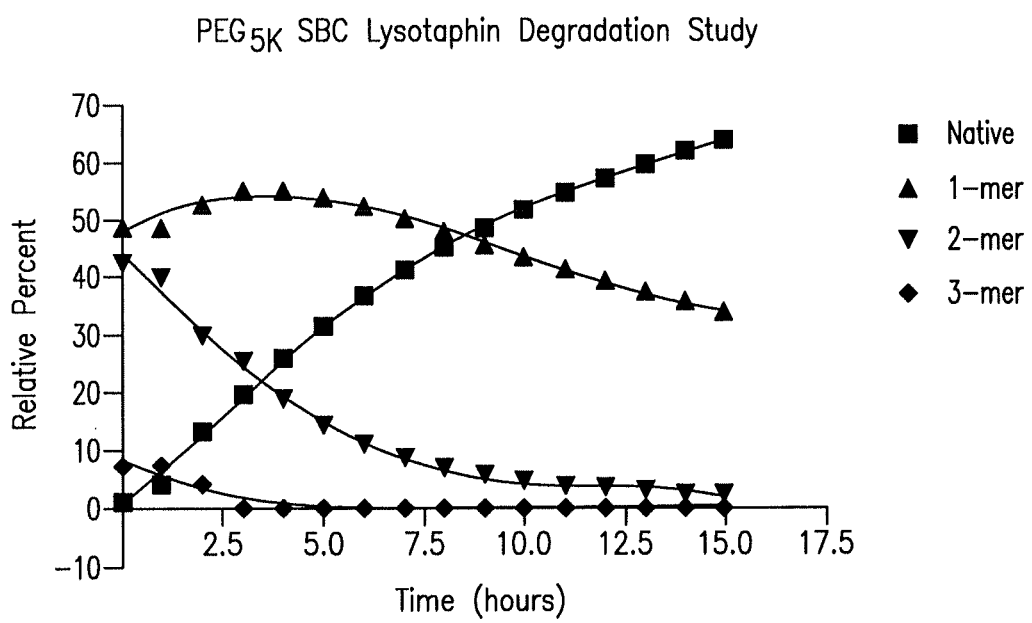
FIG. 4 is a plot demonstrating the results of a degradation study of mPEG$_{5,000\ Da}$-lysostaphin, as described in Example 1.

Degradation Study of Purified Conjugate. An in vitro release study was performed on the purified conjugate. The test was performed on an Agilent 1100 HPLC with a thermostatted autosampler. The reverse phase method described above was used to analyze the release of the native lysostaphin. The autosampler was set to 37° C. to simulate body temperature. The mPEG$_{5,000}$ $_{Da}$-lysostaphin (Conjugate A$_{5k, pH\ 6.95}$) 1-mer solution (1.1 mg/mL) was diluted 1:10 into 1×PBS (phosphate buffered saline) buffer, pH 7.35. It was incubated at 37° C. for one hour prior to the first injection. Time 0 was assumed to be before the dilution with PBS, so the HPLC results from the 1-mer conjugate were used. A sample was injected every hour for 15 hours. The compiled results are shown in FIG. 4.

The relative percentage of each component in the sample at each time point was plotted using PRISM™ software (Prism Software Corporation, Irvine Calif.). The data was fitted to a polynomial equation, and this equation was used to estimate a half-life of 17.5 hours for the mPEG$_{5,000}$ $_{Da}$-lysostaphin (Conjugate A$_{5k, pH\ 6.95}$) 1-mer component.

Example 2

PEGylation of Lysostaphin with mPEG SPC at pH 6.95

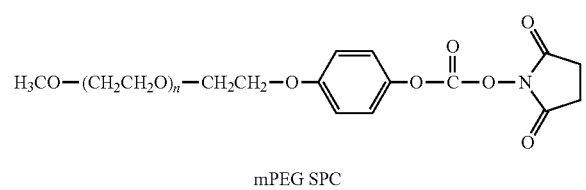

mPEG SPC

The degradable PEG reagent, mPEG SPC, having a weight average molecular weight of 20,000, was warmed from −20° C. to room temperature in a dessicator. A 3.913 mL aliquot of lysostaphin was removed from the stock solution (lot #231-01-001, 2.3 mg/mL in a 50 mM sodium phosphate buffer, pH 6.95). mPEG SPC (33.0 mg) was measured and quickly dissolved in 330 μL 2 mM HCl to form a mPEG SPC solution. The mPEG SPC solution (200 μL) was quickly added to lysostaphin. The molar ratio of PEG to protein was 3:1. After the mPEG SPC was added, the pH was 6.95. The reaction proceeded at room temperature for 10 minutes on a Rotomix (slow speed, Thermolyne) and was then quenched by the addition of 3 μL acetic acid to lower the pH to pH 5.14+/−0.2. A composition comprising a degradable conjugate of mPEG$_{20,000}$ $_{Da}$-lysostaphin (Conjugate B$_{20k, pH\ 6.95}$) was formed. A structural representation of the 1-mer version of the mPEG$_{20,000}$ $_{Da}$-lysostaphin (Conjugate B$_{20k, pH\ 6.95}$) prepared in accordance with this example is provided below (wherein "—NH-LY" represents a residue of lysostaphin).

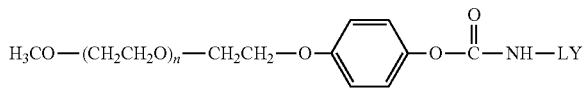

Figure 5:
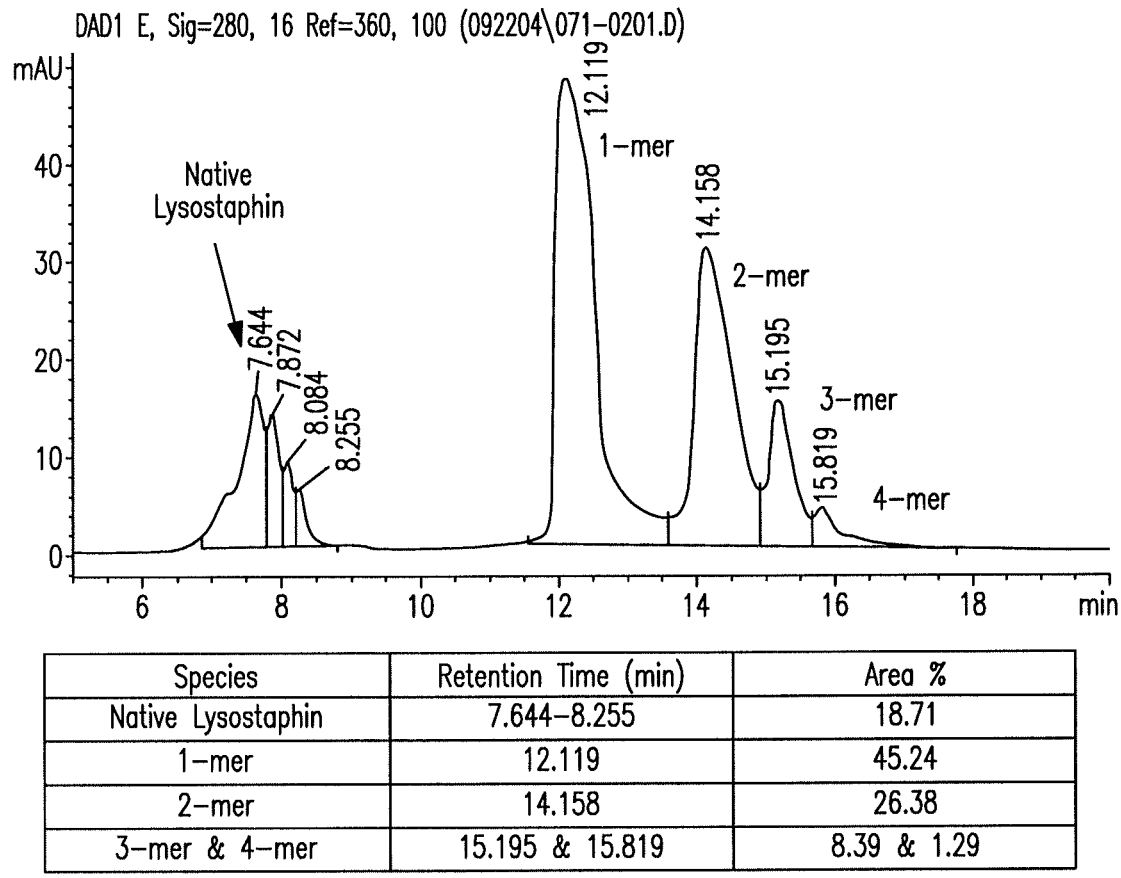
FIG. 5 corresponds to the results of a reverse phase HPLC analysis of mPEG$_{20,000\ Da}$-lysostaphin PEGylation reaction mixture, as described in Example 2.

According to reverse phase chromatography, the PEGylation yield of mono-PEGylated conjugate ("1-mer") is ~45.2% (results shown in FIG. 5).

In order to purify the composition comprising mPEG$_{20,000}$ $_{Da}$-lysostaphin (Conjugate B$_{20k, pH\ 6.95}$), a HiTrap SP HP Sepharose cation exchange column (5 mL, Amersham Biosciences, cat. 17-1152-01, lot #298974) was used with an FPLC (Pharmacia). The start buffer was 25 mM HAc/NaAc, pH 5.3, and the elution buffer was 25 mM HAc/NaAc with 500 mM NaCl, pH 5.3. The flow rate was 3 mL/min, and the sample loading range was 2.3 to 5 mg lysostaphin. Table 5 lists a summary of the purification gradients used.

TABLE 5

Purification for mPEG$_{20,000\ Da}$-Lysostaphin (Conjugate B$_{20k, pH\ 6.95}$)

| Volume (ml) | % B |
| --- | --- |
| 0 | 0 |
| 25 | 0 |
| 35 | 23 |
| 55 | 23 |
| 65 | 33 |
| 85 | 33 |
| 90 | 100 |
| 110 | 100 |
| 115 | 0 |
| 135 | 0 |

With this method, the 2- and higher-mers elute at 115 mM NaCl. The 1-mer conjugate elutes at 165 mM NaCl. There is little carryover of 2-mer into the 1-mer peak and no significant native contamination. There is, however, a small amount of 1-mer conjugate that is detected by HPLC in the native peak and the high-mer peak.

Figure 6:
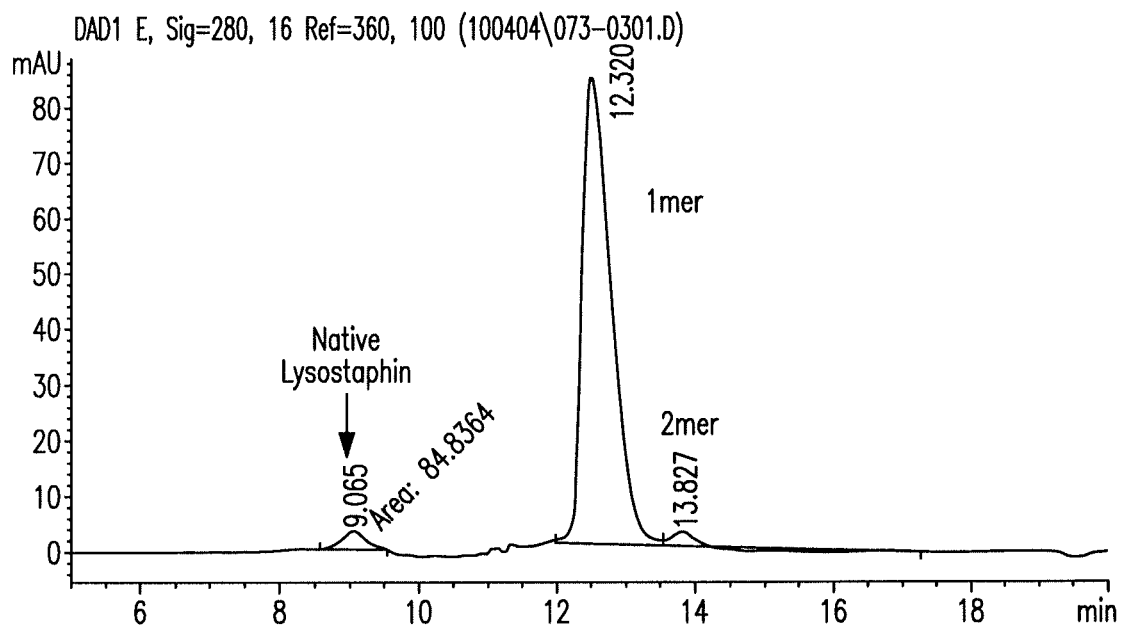
FIG. 6 corresponds to the results of a reverse phase HPLC analysis of a mPEG$_{20,000\ Da}$-lysostaphin product, as described in Example 2.
Figure 7:
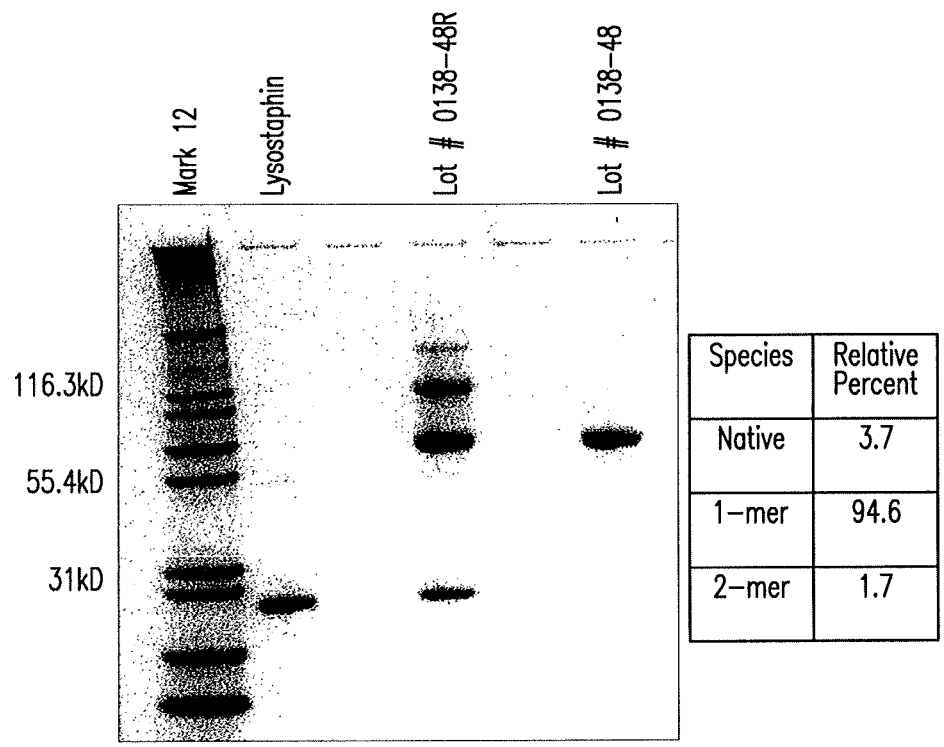
FIG. 7 represents a SDS-PAGE analysis of mPEG$_{20,000\ Da}$-lysostaphin reaction mixture prepared as described in Example 2. Lane 1: Invitrogen Mark 12 unstained standard: Lane 2: lysostaphin standard. Lane 3: 0138-48R reaction mixture. Lane 4: 0138-48 purified mono-PEGylated conjugate.

The now purified mPEG$_{20,000}$ $_{Da}$-lysostaphin (Conjugate B$_{20k, pH\ 6.95}$) produced from the PEGylation of lysostaphin with mPEG SPC at pH 6.95 was characterized and was analyzed by reverse phase chromatography (results shown in FIG. 6) and SDS-PAGE gel electrophoresis (results shown in FIG. 7). As shown in FIG. 6, the purified mono-PEGylated conjugate was ~94% pure with less than 4% each of contaminating native protein or di-PEGylated conjugate. FIG. 7 shows the purity of the mono-conjugate as analyzed by SDS-PAGE. Lane 1 contains the molecular weight standards. Native lysostaphin, the initial reaction mixture (0138-48R) and the purified mono-PEGylated conjugate (138-48) are shown in the subsequent lanes. Gel scanning analysis yielded a purity of ~95% for the mono-PEGylated conjugate. **SM0138-48R is the reaction mixture. SM0138-48 is the purified conjugate. The native percentage in the gel analysis is slightly higher than the HPLC result because of the labile nature of the conjugate and the high pH of the electrophoresis buffers.

Concentration and Buffer Exchange. A YM3 ultrafiltration membrane was equilibrated in milli-Q water for one hour with three exchanges of water. It was then mounted in an ultrafiltration unit (50 mL stirred cell, model 8050, Amicon). The purified PEG-lysostaphin 1-mer solution was transferred into the unit. The ultrafiltration unit was capped and connected to the N$_2$ gas line at a pressure of 55 psi. The purified solution was concentrated over a four hour period until the volume was reduced to ~2.3 mL. The conjugate remained in the purification buffer at pH 5.3 due to the instability of the degradable conjugate at higher pH. The product concentration was measured at UV 280 nm. The final concentration of the protein conjugate was 1.06 mg/mL.

Figure 8:
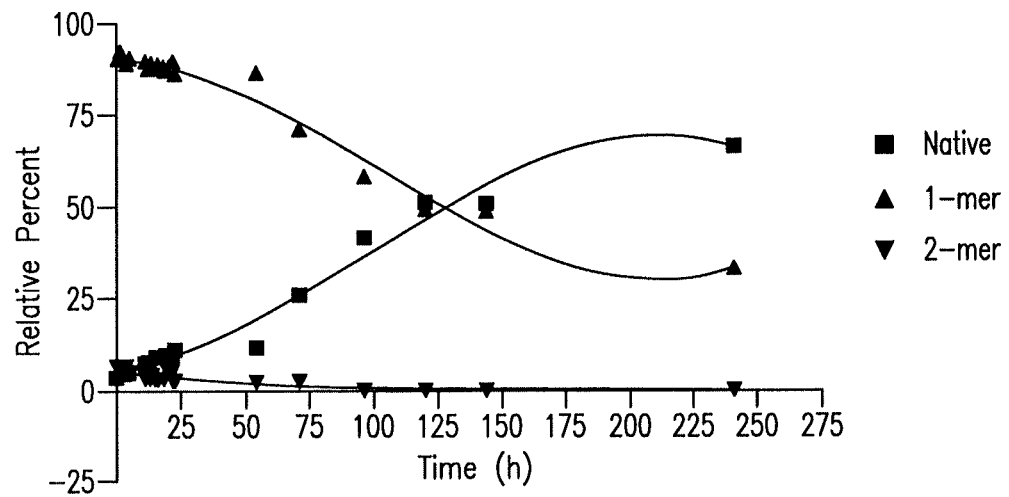
FIG. 8 is a plot demonstrating the results of a degradation study of mPEG$_{20,000\ Da}$-lysostaphin PEGylation, as described in Example 2.

Degradation Study of Purified Conjugate. An in vitro release study was performed on the purified conjugate. The test was performed on an Agilent 1100 HPLC with a thermostatted autosampler. A reverse phase method was used to analyze the release of the native protein. The autosampler was set to 37° C. to simulate body temperature. The 1-mer conjugate (1.06 mg/mL) was diluted 1:10 into 1×PBS buffer, pH 7.35. It was incubated at 37° C. over the course of the study. A sample was injected every hour for 24 hours followed by once a day injections for 10 days. The conjugate was kept in a 37° C. incubator when not being analyzed. The compiled results are shown in FIG. 8.

The relative percentage of each component in the sample at each time point was plotted using PRISM™ software (Prism Software Corporation, Irvine Calif.). The data was fitted to a polynomial equation, and this equation was used to estimate a half-life of approximately 130 hours for the 1-mer conjugate.

Example 3

PEGylation of Lysostaphin with mPEG SBC at pH 5.6

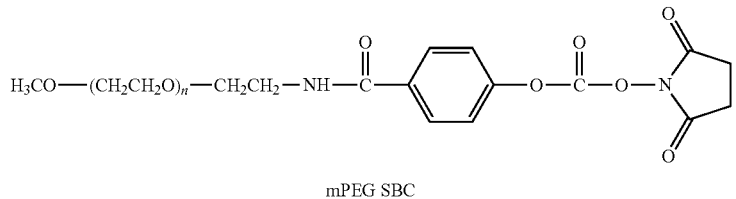

mPEG SBC

The degradable PEG reagent, mPEG SBC having a weight average molecular weight of 30,000 Daltons, was warmed from −20° C. to room temperature in a dessicator. Lysostaphin (299.2 mg) was measured and dissolved in a 50 mM sodium phosphate buffer, pH 5.6) to make a 2 mg/mL solution. mPEG SBC (1.67 g) was measured and dissolved in 37.5 mL DMSO to form an mPEG SBC solution. The mPEG SBC solution was heated at 40° C. until the mPEG SBC was dissolved. The solution was allowed to cool back down to room temperature. The mPEG SBC solution (37.5 mL) was infused into the stirred lysostaphin solution at a rate of 4.6 mL/min. The molar ratio of mPEG SBC to protein was 5:1. The reaction proceeded at room temperature for 10 minutes with stirring. The reaction was diluted 1:3 with the purification buffer, 20 mM sodium acetate, pH 5.3, in preparation for purification. A composition comprising a degradable conjugate of mPEG$_{30,000\ Da}$-lysostaphin (Conjugate A$_{30k,\ pH\ 5.6}$) was formed. A structural representation of the 1-mer version of the mPEG$_{30,000\ Da}$-lysostaphin (Conjugate A$_{30k,\ pH\ 5.6}$) prepared in accordance with this example is provided below (wherein "—NH-LY" represents a residue of lysostaphin).

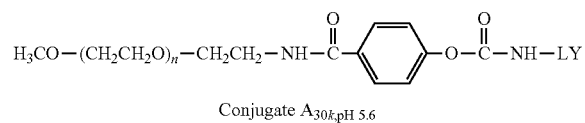

Conjugate A$_{30k}$,pH 5.6

Figure 9:
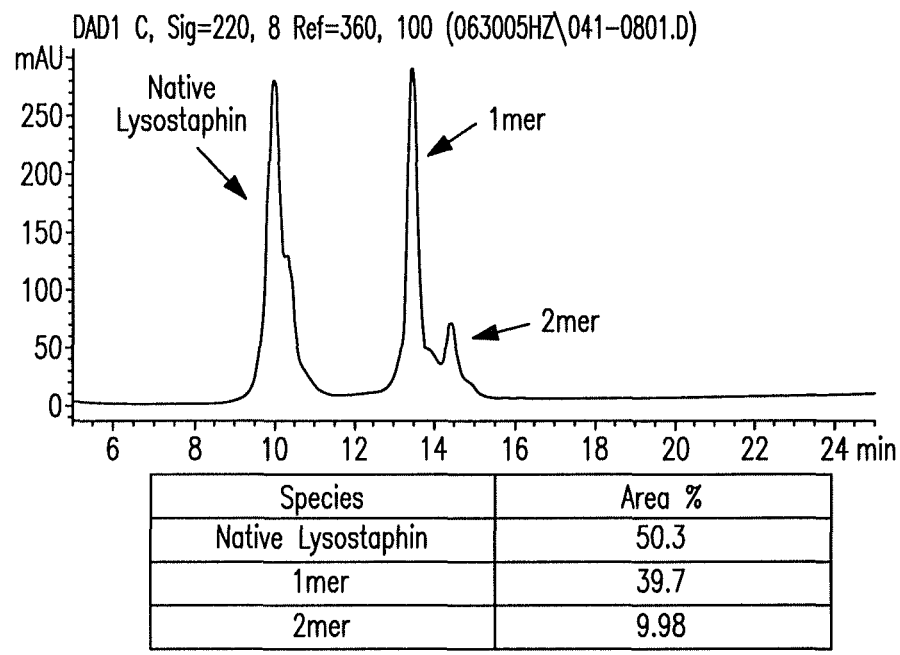
FIG. 9 corresponds to the results of a reverse phase HPLC analysis of mPEG$_{30,000\ Da}$-lysostaphin PEGylation reaction mixture, as described in Example 3.

According to reverse phase chromatography, the PEGylation reaction yield of mono-PEGylated conjugate (the "1-mer") is ~39.7% (results shown in FIG. 9).

In order to purify the composition comprising mPEG$_{30,000\ Da}$-lysostaphin (Conjugate A$_{30k,\ pH\ 5.6}$)) Toyopearl SP650s resin (Tosoh Bioscience, part #14698) was packed into a 4.4 cm diameter column with a bed volume of 300 mL. The start buffer was 20 mM sodium acetate, pH 5.3, and the elution buffer was 20 mM HAc/NaAc with 500 mM NaCl, pH 5.3. The flow rate was 40 mL/min, and the sample loading range was 300-1,500 mg lysostaphin. Table 6 presents a summary of purification gradients used.

TABLE 6

Purification Methods for mPEG$_{30,000\ Da}$-Lysostaphin (Conjugate A$_{30k,\ pH\ 5.6}$)

| Column volume | % B |
|---|---|
| 0 | 0 |
| 2 | 0 |
| 3 | 19 |
| 6 | 19 |
| 9 | 29 |
| 13 | 29 |

TABLE 6-continued

Purification Methods for mPEG$_{30,000\ Da}$-Lysostaphin (Conjugate A$_{30k,\ pH\ 5.6}$)

| Column volume | % B |
|---|---|
| 15 | 100 |
| 16 | 100 |

Because there was not complete separation of the native ("unconjugated") lysostaphin, improvement of the purification is warranted (although there may be certain circumstances wherein a composition comprising mixtures of conjugated and unconjugated lysostaphin might be desirable). Many 1-mer fractions had to be cut because of high native content leading to a product that has a higher 2-mer percentage in order to minimize native contamination of the conjugate.

Figure 10:
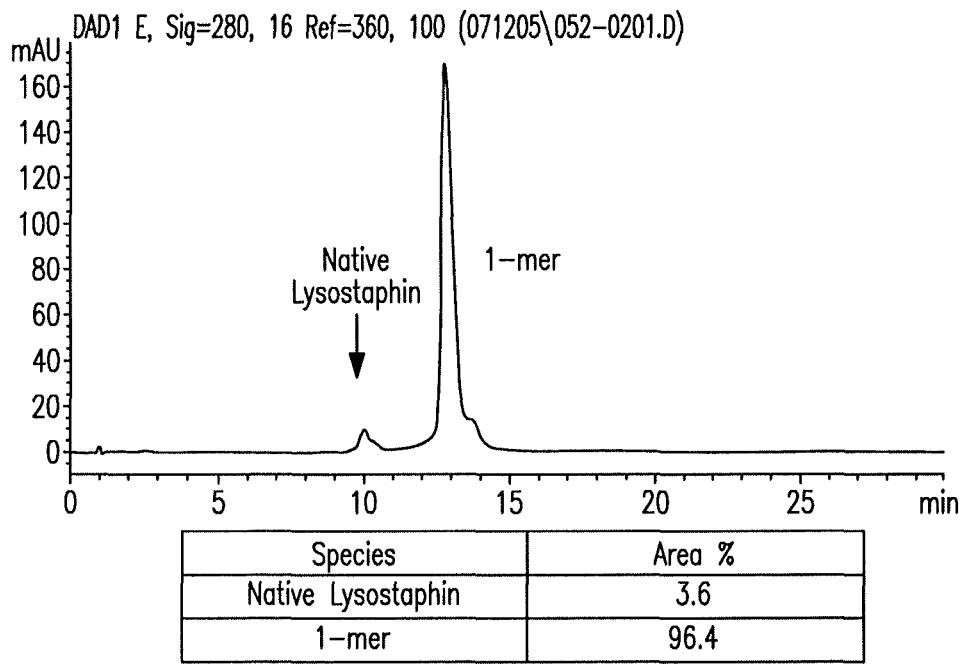
FIG. 10 corresponds to the results of a reverse phase HPLC analysis of mPEG$_{30,000\ Da}$-lysostaphin PEGylation product, as described in Example 3.
Figure 11:
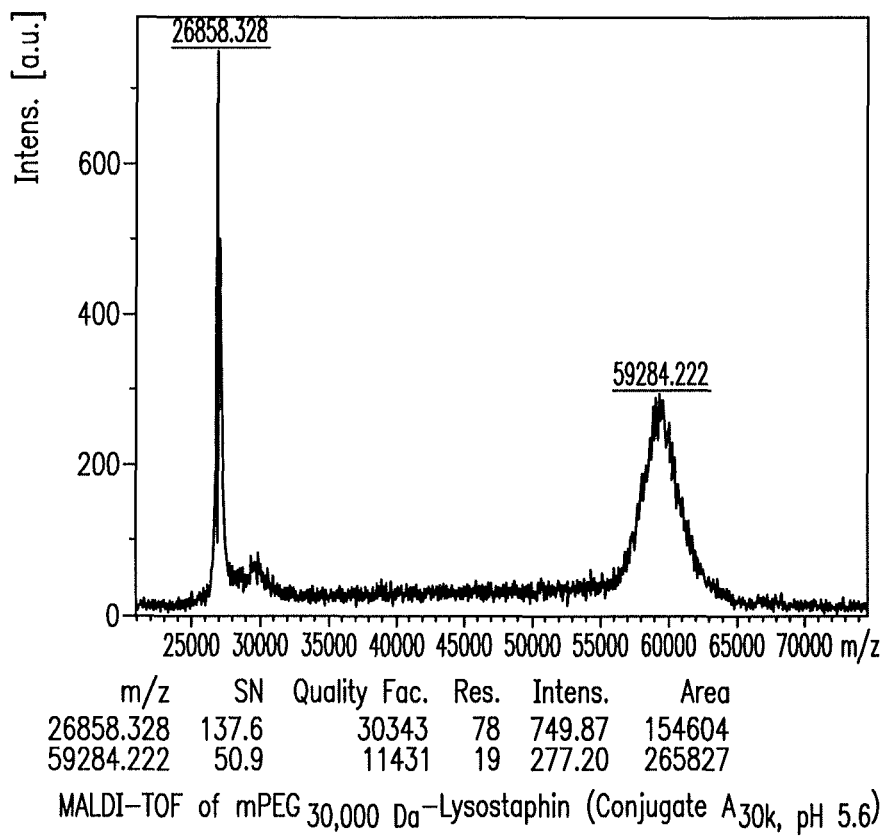
FIG. 11 corresponds to the results of a MALDI-TOF analysis of mPEG$_{30,000\ Da}$-lysostaphin PEGylation product, as described in Example 3.

The now purified mPEG$_{30,000\ Da}$-Lysostaphin (Conjugate A$_{30k,\ pH\ 5.6}$) produced from the PEGylation of lysostaphin with mPEG SBC at pH 5.6 was characterized and was analyzed by reverse-phase chromatography (results shown in FIG. 10). According to the reverse phase analysis, the mono-conjugate ("1-mer") was 96.4% pure with a small amount of native protein contaminant. The MALDI-TOF analysis (results shown in FIG. 11) confirmed the mono 30 kDa conjugate was formed.

Concentration. The diafiltration unit was flushed with 8 liters deionized water followed by 2 L of 20 mM sodium acetate, pH 5.3 to equilibrate the membrane. The purified 1-mer fractions were pooled and concentrated with a PALL Omega 5K MWCO Ultrasette diafiltration cassette and a peristaltic pump. The conjugate remained in the purification buffer at pH 5.3 due to the instability of the degradable conjugate at higher pH. The product concentration was determined by UV spectroscopy. The final concentration of the protein conjugate was 1.95 mg/mL.

Figure 12:
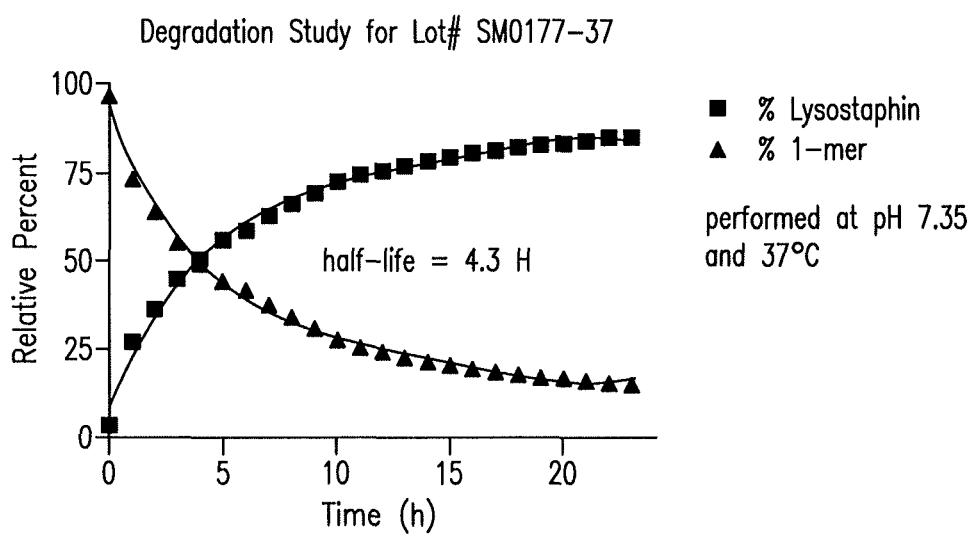
FIG. 12 is a plot demonstrating the results of a degradation study of mPEG$_{30,000\ Da}$-lysostaphin, as described in Example 4.

Degradation Study of Purified Conjugate. An in vitro release study was performed on the purified conjugate. The test was performed on an Agilent 1100 HPLC with a thermostatted autosampler. The reverse phase method described above was used to analyze the release of the native lysostaphin. The autosampler was set to 37° C. to simulate body temperature. The mPEG$_{30,000\ Da}$-Lysostaphin (Conjugate A$_{30k, pH 5.6}$) 1-mer solution (1.1 mg/mL) was diluted 1:10 into 1×PBS (phosphate buffered saline) buffer, pH 7.35. It was incubated at 37° C. for 1 hour prior to the first injection. Time 0 was assumed to be before the dilution with PBS, so the HPLC results from the 1-mer conjugate were used. A sample was injected every hour for 23 hours. The compiled results are shown in FIG. 12.

The relative percentage of each component in the sample at each time point was plotted using PRISM™ software (Prism Software Corporation, Irvine Calif.). The data was fitted to a polynomial equation, and this equation was used to estimate a half-life of 4.3 hours for the mPEG$_{30,000\ Da}$-Lysostaphin (Conjugate A$_{30k, pH 5.6}$) 1-mer component.

Example 4

PEGylation of Lysostaphin with mPEG SBC at pH 6.9

$$H_3CO-(CH_2CH_2O)_n-CH_2CH_2-NH-\overset{O}{\underset{\|}{C}}-\underset{}{\phantom{x}}\!\!\!\!\bigcirc\!\!\!\!\phantom{x}-O-\overset{O}{\underset{\|}{C}}-O-N\underset{}{\phantom{x}}$$

mPEG SBC

The degradable PEG reagent, mPEG SBC having a weight average molecular weight of 30,000 Daltons, was warmed from −20° C. to room temperature in a dessicator. Lysostaphin (299.2 mg) was measured and dissolved in a 50 mM sodium phosphate buffer, pH 6.9) to make a 2 mg/mL solution. mPEG SBC (1.3 g) was measured and dissolved in 37.5 mL DMSO to form an mPEG SBC solution. The mPEG SBC solution was heated at 40° C. until the mPEG SBC was dissolved. The solution was allowed to cool back down to room temperature. The mPEG SBC solution (37.5 mL) was infused into the stirred lysostaphin solution at a rate of 5 mL/min. The molar ratio of mPEG SBC to protein was 4:1. The reaction proceeded at room temperature for 15 minutes with stirring. The reaction was quenched by the addition of 300 μL acetic acid to drop the pH to 5.34. A composition comprising a degradable conjugate of mPEG$_{30,000\ Da}$-lysostaphin (Conjugate A$_{30k, pH 6.9}$) was formed. A structural representation of the 1-mer version of the mPEG$_{30,000\ Da}$-lysostaphin (Conjugate A$_{30k, pH 6.9}$) prepared in accordance with this example is provided below (wherein "—NH-LY" represents a residue of lysostaphin).

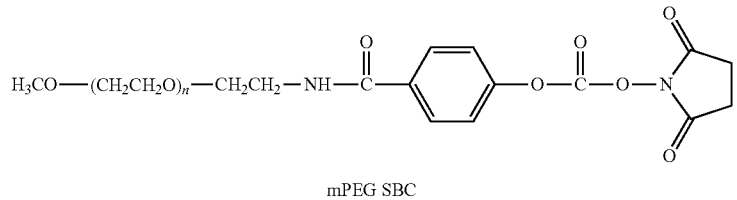

Conjugate A$_{30k, pH 6.9}$

Figure 13:
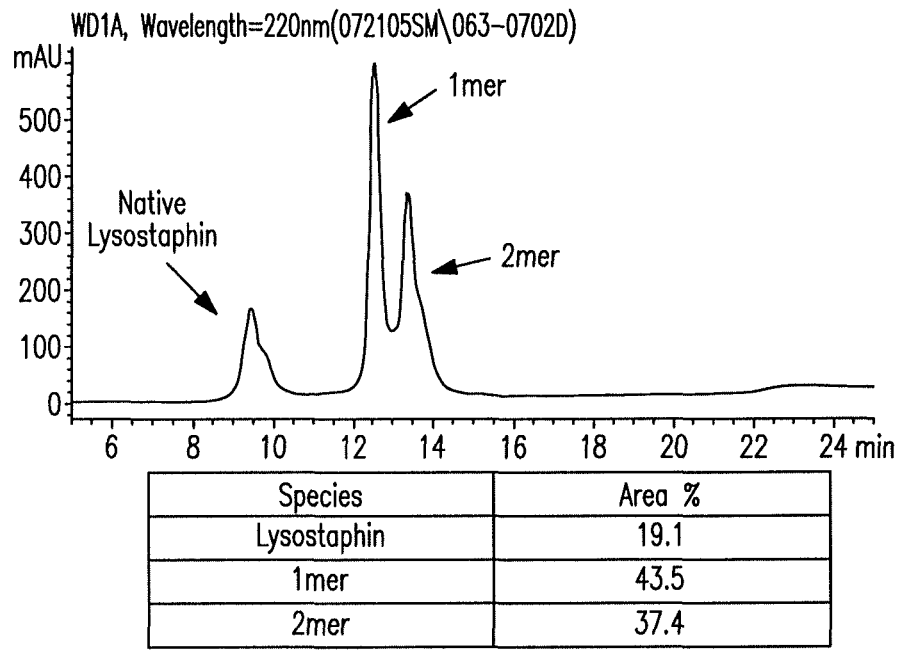
FIG. 13 corresponds to the results of a reverse phase HPLC analysis of mPEG$_{30,000\ Da}$-lysostaphin PEGylation reaction mixture, as described in Example 4.

According to reverse phase chromatography, the PEGylation reaction yield of mono-PEGylated conjugate (the "1-mer") is ~43.5% and di-PEGylated conjugate (the "2-mer") is ~37.4% (results shown in FIG. 13).

In order to purify the composition comprising mPEG$_{30,000\ Da}$-lysostaphin (Conjugate A$_{30k, pH 6.9}$), Toyopearl SP650s resin (Tosoh Bioscience, part #14698) was packed into a 4.4 cm diameter column with a bed volume of 300 mL. The start buffer was 20 mM sodium acetate, pH 5.3, and the elution buffer was 20 mM HAc/NaAc with 500 mM NaCl, pH 5.3. The flow rate was 40 mL/min, and the sample loading range was 300-1,500 mg lysostaphin. Table 7 presents a summary of purification gradients used.

TABLE 7

Purification Methods for mPEG$_{30,000\ Da}$-Lysostaphin (Conjugate A$_{30k, pH 6.9}$)

| Column volume | % B |
|---|---|
| 0 | 0 |
| 2 | 0 |
| 3 | 19 |
| 6 | 19 |
| 9 | 29 |

TABLE 7-continued

Purification Methods for mPEG$_{30,000\ Da}$-Lysostaphin (Conjugate A$_{30k, pH 6.9}$)

| Column volume | % B |
|---|---|
| 13 | 29 |
| 15 | 100 |
| 16 | 100 |

Figure 14:
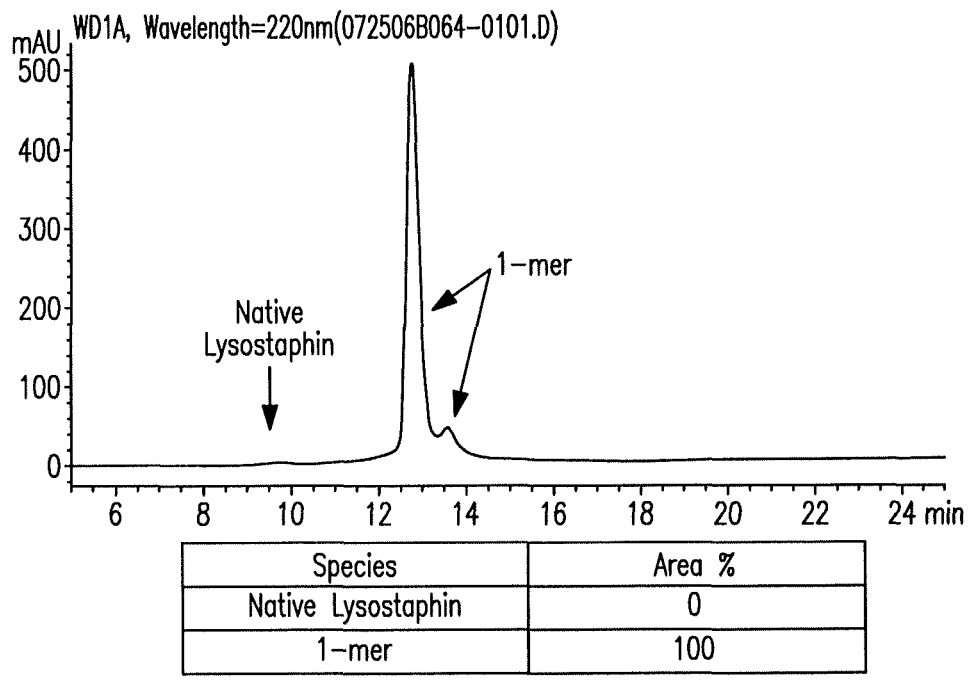
FIG. 14 corresponds to the results of a reverse phase HPLC analysis of mPEG$_{30,000\ Da}$-lysostaphin PEGylation product, as described in Example 4.
Figure 15:
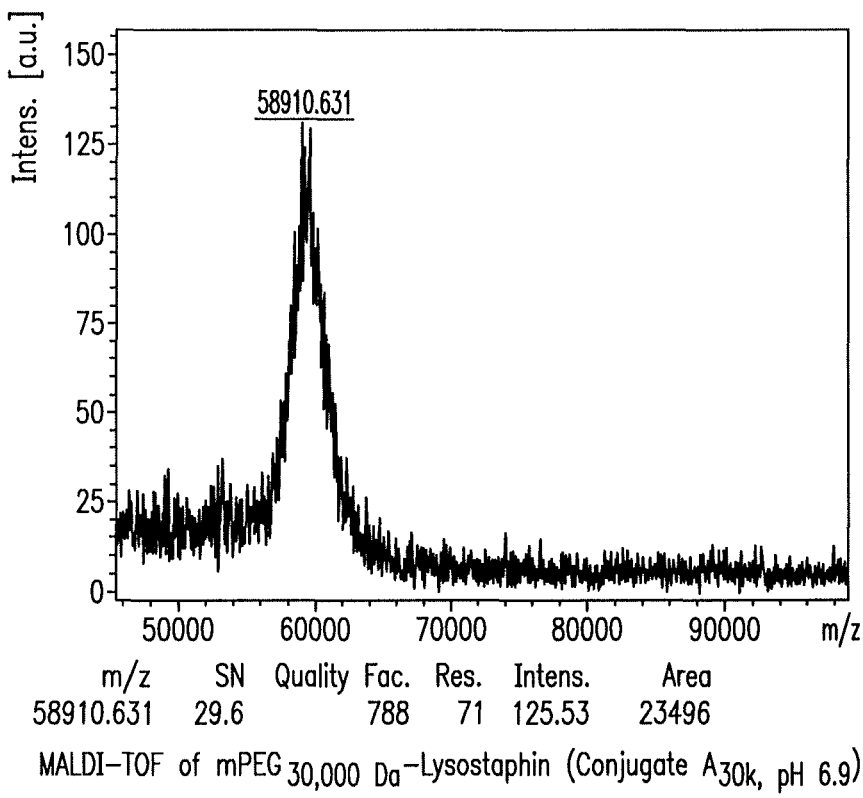
FIG. 15 corresponds to the results of a MALDI-TOF analysis of mPEG$_{30,000\ Da}$-lysostaphin PEGylation product, as described in Example 4.

Upon purification, the mPEG$_{30,000\ Da}$-Lysostaphin (Conjugate A$_{30k, pH 6.9}$) produced from the PEGylation of lysostaphin with mPEG SBC at pH 6.9 was characterized and quantified and found to be 100% pure (within detection limits). Using the gradient in Table 7, all of the native protein was separated. Note the shoulder at the back of the main 1-peak in FIG. 14 (results of reverse phase HPLC). This is also a mono-PEGylated conjugate (confirmed by SDS-PAGE analysis, results not shown) but is likely a different positional isomer with a slightly different charge. The final purified mono-PEGylated conjugate was also analyzed by MALDI-TOF (results shown in FIG. 15).

Concentration. The diafiltration unit was flushed with 8 L deionized water followed by 2 L of 20 mM sodium acetate, pH 5.3 to equilibrate the membrane. The purified 1-mer fractions were pooled and concentrated with a PALL Omega 5K MWCO Ultrasette diafiltration cassette and a peristaltic pump. The conjugate remained in the purification buffer at pH 5.3 due to the instability of the degradable conjugate at higher pH. The product concentration was determined by UV spectroscopy. The final concentration of the protein conjugate was 2.36 mg/mL.

Figure 16:
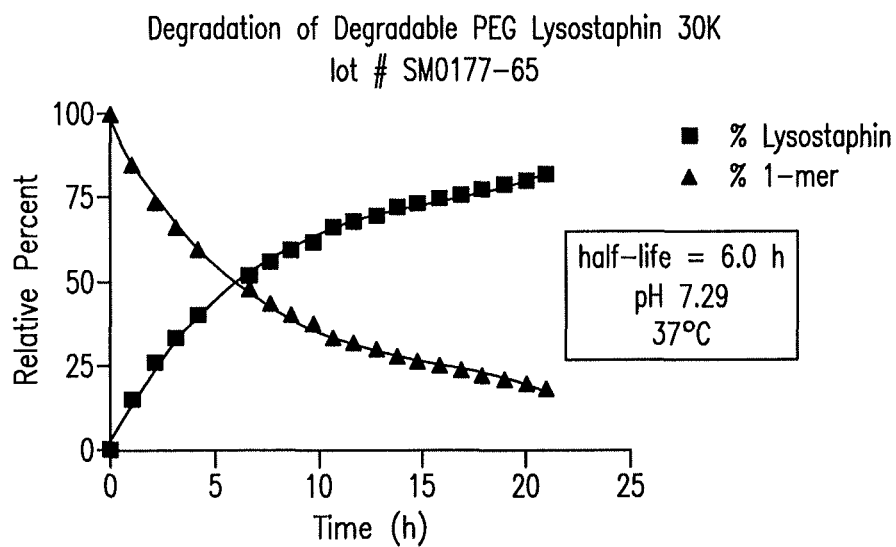
FIG. 16 is a plot demonstrating the results of a degradation study of mPEG$_{30,000\ Da}$-lysostaphin, as described in Example 4.

Degradation Study of Purified Conjugate. An in vitro release study was performed on the purified conjugate. The test was performed on an Agilent 1100 HPLC with a thermostatted autosampler. The reverse phase method described above was used to analyze the release of the native lysostaphin. The autosampler was set to 37° C. to simulate body temperature. The $mPEG_{30,000\ Da}$-Lysostaphin (Conjugate $A_{30k,pH\ 6.9}$) 1-mer solution (1.1 mg/mL) was diluted 1:10 into 1×PBS (phosphate buffered saline) buffer. The pH of the solution was checked and found to be pH 7.29. It was incubated at 37° C. for 1 hour prior to the first injection. Time 0 was assumed to be before the dilution with PBS, so the HPLC results from the 1-mer conjugate were used. A sample was injected every 1.4 hours for 21 hours. The compiled results are shown in FIG. 16.

The relative percentage of each component in the sample at each time point was plotted using PRISM™ software (Prism Software Corporation, Irvine Calif.). The data was fitted to a polynomial equation, and this equation was used to estimate a half-life of 6.0 hours for the $mPEG_{30,000\ Da}$-Lysostaphin (Conjugate $A_{30k,pH\ 6.9}$) 1-mer component.

Examples 5-12

Examples 1, 2, 3, and 4 were repeated with preprolysostaphin and prolysostaphin. Similar results of successful conjugation are obtained.

---

What is claimed is:

1. A pharmaceutical composition comprising:

(i) a conjugate selected from the group consisting of

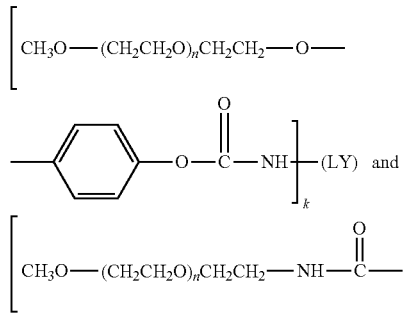

and

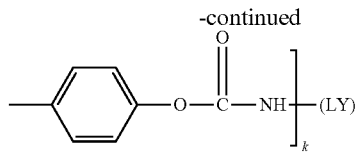

wherein, in each case, (LY) is a residue of lysostaphin, k is one, and (n) is defined to provide a weight average molecular weight from about 5,000 Daltons to about 85,000 Daltons, and (ii) a pharmaceutically acceptable excipient.

2. The pharmaceutical composition of claim 1, wherein the weight average molecular weight is from about 15,000 Daltons to about 40,000 Daltons.

3. The pharmaceutical composition of claim 2, wherein the weight average molecular weight is about 30,000 Daltons.

* * * * *

SEQUENCE LISTING

```
<160> NUMBER OF SEQ ID NOS: 1

<210> SEQ ID NO 1
<211> LENGTH: 389
<212> TYPE: PRT
<213> ORGANISM: Staphylococcus simulans

<400> SEQUENCE: 1

Met Lys Lys Thr Lys Asn Asn Tyr Tyr Thr Arg Pro Leu Ala Ile Gly
1               5                   10                  15

Leu Ser Thr Phe Ala Leu Ala Ser Ile Val Tyr Gly Gly Ile Gln Asn
                20                  25                  30

Glu Thr His Ala Ser Glu Lys Ser Asn Met Asp Val Ser Lys Lys Val
            35                  40                  45

Ala Glu Val Glu Thr Ser Lys Ala Pro Val Glu Asn Thr Ala Glu Val
        50                  55                  60

Glu Thr Ser Lys Ala Pro Val Glu Asn Thr Ala Glu Val Glu Thr Ser
65                  70                  75                  80

Lys Ala Pro Val Glu Asn Thr Ala Glu Val Glu Thr Ser Lys Ala Pro
                85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Leu Val Gln Asn Arg Thr Ala Leu Arg Ala
    130                 135                 140

Ala Thr His Glu His Ser Ala Gln Trp Leu Asn Asn Tyr Lys Lys Gly
145                 150                 155                 160

Tyr Gly Tyr Gly Pro Tyr Pro Leu Gly Ile Asn Gly Gly Met His Tyr
                165                 170                 175

Gly Val Asp Phe Phe Met Asn Ile Gly Thr Pro Val Lys Ala Ile Ser
            180                 185                 190

Ser Gly Lys Ile Val Glu Ala Gly Trp Ser Asn Tyr Gly Gly Gly Asn
        195                 200                 205
```

```
Gln Ile Gly Leu Ile Glu Asn Asp Gly Val His Arg Gln Trp Tyr Met
    210                 215                 220
His Leu Ser Lys Tyr Asn Val Lys Val Gly Asp Tyr Val Lys Ala Gly
225                 230                 235                 240
Gln Ile Ile Gly Trp Ser Gly Ser Thr Gly Tyr Ser Thr Ala Pro His
                245                 250                 255
Leu His Phe Gln Arg Met Val Asn Ser Phe Ser Asn Ser Thr Ala Gln
            260                 265                 270
Asp Pro Met Pro Phe Leu Lys Ser Ala Gly Tyr Gly Lys Ala Gly Gly
        275                 280                 285
Thr Val Thr Pro Thr Pro Asn Thr Gly Trp Lys Thr Asn Lys Tyr Gly
    290                 295                 300
Thr Leu Tyr Lys Ser Glu Ser Ala Ser Phe Thr Pro Asn Thr Asp Ile
305                 310                 315                 320
Ile Thr Arg Thr Thr Gly Pro Phe Arg Ser Met Pro Gln Ser Gly Val
                325                 330                 335
Leu Lys Ala Gly Gln Thr Ile His Tyr Asp Glu Val Met Lys Gln Asp
            340                 345                 350
Gly His Val Trp Val Gly Tyr Thr Gly Asn Ser Gly Gln Arg Ile Tyr
        355                 360                 365
Leu Pro Val Arg Thr Trp Asn Lys Ser Thr Asn Thr Leu Gly Val Leu
    370                 375                 380
Trp Gly Thr Ile Lys
385
```